(12) United States Patent
Harris, Sr. et al.

(10) Patent No.: US 8,321,243 B1
(45) Date of Patent: Nov. 27, 2012

(54) SYSTEMS AND METHODS FOR THE INTELLIGENT COORDINATION OF BENEFITS IN HEALTHCARE TRANSACTIONS

(75) Inventors: Patrick Harris, Sr., Atlanta, GA (US); Roger Pinsonneault, Alpharetta, GA (US)

(73) Assignee: McKesson Financial Holdings Limited (BM)

( * ) Notice: Subject to any disclaimer, the term of this patent is extended or adjusted under 35 U.S.C. 154(b) by 277 days.

(21) Appl. No.: 12/705,921

(22) Filed: Feb. 15, 2010

(51) Int. Cl.
*G06F 19/00* (2011.01)
(52) U.S. Cl. .......................................................... 705/3
(58) Field of Classification Search .................. 705/2, 3, 705/4
See application file for complete search history.

(56) References Cited

U.S. PATENT DOCUMENTS

| | | | |
|---|---|---|---|
| 4,674,041 A | 6/1987 | Lemon et al. |
| 4,723,212 A | 2/1988 | Mindrum et al. |
| 4,910,672 A | 3/1990 | Off et al. |
| 5,007,641 A | 4/1991 | Seidman |
| 5,080,364 A | 1/1992 | Seidman |
| 5,173,851 A | 12/1992 | Off et al. |
| 5,201,010 A | 4/1993 | Deaton et al. |
| 5,235,702 A | 8/1993 | Miller |
| 5,237,620 A | 8/1993 | Deaton et al. |
| 5,301,105 A | 4/1994 | Cummings |
| 5,305,196 A | 4/1994 | Deaton et al. |
| 5,327,508 A | 7/1994 | Deaton et al. |
| 5,359,509 A | 10/1994 | Little et al. |
| 5,388,165 A | 2/1995 | Deaton et al. |
| 5,430,644 A | 7/1995 | Deaton et al. |
| 5,448,471 A | 9/1995 | Deaton et al. |
| 5,544,044 A | 8/1996 | Leatherman |
| 5,550,734 A | 8/1996 | Tarter et al. |
| 5,588,649 A | 12/1996 | Blumberg et al. |
| 5,592,560 A | 1/1997 | Deaton et al. |
| 5,612,868 A | 3/1997 | Off et al. |
| 5,621,812 A | 4/1997 | Deaton et al. |
| 5,628,530 A | 5/1997 | Thornton |
| 5,638,457 A | 6/1997 | Deaton et al. |
| 5,642,485 A | 6/1997 | Deaton et al. |
| 5,644,723 A | 7/1997 | Deaton et al. |
| 5,644,778 A | 7/1997 | Burks et al. |

(Continued)

FOREIGN PATENT DOCUMENTS

CA 2482370 A1 3/2006

(Continued)

OTHER PUBLICATIONS

"Medi-Cal POS NCPDP Pharmacy transaction Specifications Third Party Vendors"; May 2005.*

(Continued)

*Primary Examiner* — John Pauls
(74) *Attorney, Agent, or Firm* — Sutherland Asbill & Brennan LLP

(57) ABSTRACT

Systems and methods are provided for the coordination of benefits. The systems and methods may include receiving a healthcare claim request from a healthcare provider computer; determining, based at least in part from patient information in the healthcare transaction claim request, that the patient is associated with at least a first payer and a second payer; generating a primary claim request based upon the identified product and the patient associated with the healthcare claim request, the primary claim associated with the first payer; and generating a coordination of benefits (COB) claim request based at least in part on the received first adjudicated reply associated with the primary claim request, the COB claim request, the COB claim request associated with a second payer.

13 Claims, 5 Drawing Sheets

U.S. PATENT DOCUMENTS

| | | | |
|---|---|---|---|
| 5,649,114 A | 7/1997 | Deaton et al. |
| 5,659,469 A | 8/1997 | Deaton et al. |
| 5,675,662 A | 10/1997 | Deaton et al. |
| 5,687,322 A | 11/1997 | Deaton et al. |
| 5,704,044 A | 12/1997 | Tarter et al. |
| 5,748,907 A | 5/1998 | Crane |
| 5,749,907 A | 5/1998 | Mann |
| 5,832,447 A | 11/1998 | Rieker et al. |
| 5,832,457 A | 11/1998 | O'Brien |
| 5,845,255 A | 12/1998 | Mayaud |
| 5,857,175 A | 1/1999 | Day et al. |
| 5,892,827 A | 4/1999 | Beach et al. |
| 5,892,900 A | 4/1999 | Ginter et al. |
| 5,915,007 A | 6/1999 | Klapka |
| 5,926,795 A | 7/1999 | Williams |
| 5,950,169 A | 9/1999 | Borghesi et al. |
| 5,956,736 A | 9/1999 | Hanson et al. |
| 5,963,915 A | 10/1999 | Kirsch |
| 5,970,469 A | 10/1999 | Scroggie et al. |
| 5,974,399 A | 10/1999 | Giuliani et al. |
| 5,991,750 A | 11/1999 | Watson |
| 6,006,242 A | 12/1999 | Poole et al. |
| 6,012,035 A | 1/2000 | Freeman, Jr. et al. |
| 6,014,634 A | 1/2000 | Scroggie et al. |
| 6,021,392 A | 2/2000 | Lester et al. |
| 6,026,370 A | 2/2000 | Jermyn |
| 6,041,309 A | 3/2000 | Laor |
| 6,055,573 A | 4/2000 | Gardenswartz et al. |
| 6,067,069 A | 5/2000 | Krause |
| 6,067,524 A | 5/2000 | Byerly et al. |
| 6,073,104 A | 6/2000 | Field |
| 6,185,541 B1 | 2/2001 | Scroggie et al. |
| 6,195,612 B1 | 2/2001 | Pack-Harris |
| 6,202,923 B1 | 3/2001 | Boyer et al. |
| 6,205,455 B1 | 3/2001 | Umen |
| 6,208,973 B1 | 3/2001 | Boyer et al. |
| 6,224,387 B1 | 5/2001 | Jones |
| 6,240,394 B1 | 5/2001 | Uecker |
| 6,260,758 B1 | 7/2001 | Blumberg |
| 6,278,979 B1 | 8/2001 | Williams |
| 6,282,516 B1 | 8/2001 | Giuliani |
| 6,298,330 B1 | 10/2001 | Gardenswartz et al. |
| 6,304,849 B1 | 10/2001 | Uecker et al. |
| 6,307,940 B1 | 10/2001 | Yamamoto et al. |
| 6,307,958 B1 | 10/2001 | Deaton et al. |
| 6,321,210 B1 | 11/2001 | O'Brien et al. |
| 6,324,516 B1 | 11/2001 | Shults et al. |
| 6,330,546 B1 | 12/2001 | Gopinathan et al. |
| 6,334,108 B1 | 12/2001 | Deaton et al. |
| 6,341,265 B1 | 1/2002 | Provost et al. |
| 6,343,271 B1 | 1/2002 | Peterson et al. |
| 6,351,735 B1 | 2/2002 | Deaton et al. |
| 6,377,935 B1 | 4/2002 | Deaton et al. |
| 6,424,949 B1 | 7/2002 | Deaton et al. |
| 6,427,020 B1 | 7/2002 | Rhoads |
| 6,484,146 B2 | 11/2002 | Day et al. |
| 6,584,448 B1 | 6/2003 | Laor |
| 6,632,251 B1 | 10/2003 | Rutten et al. |
| 6,671,692 B1 | 12/2003 | Marpe et al. |
| 6,671,693 B1 | 12/2003 | Marpe et al. |
| 6,684,195 B1 | 1/2004 | Deaton et al. |
| 6,714,918 B2 | 3/2004 | Hilmer et al. |
| 6,757,898 B1 | 6/2004 | Ilsen et al. |
| 6,769,228 B1 | 8/2004 | Mahar |
| 6,795,809 B2 | 9/2004 | O'Brien et al. |
| 6,879,959 B1 | 4/2005 | Chapman et al. |
| 6,885,994 B1 | 4/2005 | Scroggie et al. |
| 7,013,284 B2 | 3/2006 | Guyan et al. |
| 7,024,374 B1 | 4/2006 | Day et al. |
| 7,058,584 B2 | 6/2006 | Kosinski et al. |
| 7,058,591 B2 | 6/2006 | Giuliani et al. |
| 7,111,173 B1 | 9/2006 | Scheidt |
| 7,155,397 B2 | 12/2006 | Alexander et al. |
| 7,225,052 B2 | 5/2007 | Foote et al. |
| 7,228,285 B2 | 6/2007 | Hull et al. |
| 7,233,913 B2 | 6/2007 | Scroggie et al. |
| 7,309,001 B2 | 12/2007 | Banfield et al. |
| 7,356,460 B1 | 4/2008 | Kennedy et al. |
| 7,380,707 B1 | 6/2008 | Fredman |
| 7,401,027 B2 | 7/2008 | Moore et al. |
| 7,415,426 B2 | 8/2008 | Williams et al. |
| 7,418,400 B1 | 8/2008 | Lorenz |
| 7,426,480 B2 | 9/2008 | Granger et al. |
| 7,685,006 B2 | 3/2010 | Rahn et al. |
| 7,917,378 B2 | 3/2011 | Fitzgerald et al. |
| 2001/0001014 A1 | 5/2001 | Glendon, III et al. |
| 2001/0032099 A1 | 10/2001 | Joao |
| 2001/0037216 A1 | 11/2001 | Oscar et al. |
| 2001/0037224 A1 | 11/2001 | Eldridge et al. |
| 2001/0041993 A1 | 11/2001 | Campbell |
| 2002/0002495 A1 | 1/2002 | Ullman |
| 2002/0032583 A1 | 3/2002 | Joao |
| 2002/0035488 A1 | 3/2002 | Aquila et al. |
| 2002/0044043 A1 | 4/2002 | Chaco et al. |
| 2002/0049617 A1 | 4/2002 | Lencki et al. |
| 2002/0055856 A1 | 5/2002 | Adams |
| 2002/0065687 A1 | 5/2002 | Onoue |
| 2002/0087554 A1 | 7/2002 | Seelinger |
| 2002/0087583 A1 | 7/2002 | Morgan et al. |
| 2002/0111832 A1 | 8/2002 | Judge |
| 2002/0120473 A1 | 8/2002 | Wiggins |
| 2002/0128883 A1 | 9/2002 | Harris |
| 2002/0133503 A1 | 9/2002 | Amar et al. |
| 2002/0138593 A1 | 9/2002 | Novak et al. |
| 2002/0175370 A1 | 11/2002 | Bockelman |
| 2002/0183979 A1 | 12/2002 | Wildman |
| 2002/0198831 A1 | 12/2002 | Patricelli et al. |
| 2003/0009357 A1 | 1/2003 | Pish |
| 2003/0009367 A1 | 1/2003 | Morrison |
| 2003/0028404 A1 | 2/2003 | Herron et al. |
| 2003/0050799 A1 | 3/2003 | Jay et al. |
| 2003/0074218 A1 | 4/2003 | Liff et al. |
| 2003/0074222 A1 | 4/2003 | Rosow et al. |
| 2003/0083903 A1 | 5/2003 | Myers |
| 2003/0120588 A1 | 6/2003 | Dodd et al. |
| 2003/0125986 A1 | 7/2003 | Collosi |
| 2003/0149594 A1 | 8/2003 | Beazley et al. |
| 2003/0149625 A1 | 8/2003 | Leonardi et al. |
| 2003/0154163 A1 | 8/2003 | Phillips et al. |
| 2003/0229540 A1 | 12/2003 | Algiene |
| 2004/0006490 A1 | 1/2004 | Gingrich et al. |
| 2004/0019464 A1 | 1/2004 | Martucci et al. |
| 2004/0039599 A1 | 2/2004 | Fralic |
| 2004/0046020 A1 | 3/2004 | Andreasson et al. |
| 2004/0049422 A1 | 3/2004 | Mortimer |
| 2004/0054657 A1 | 3/2004 | Takeyama |
| 2004/0073457 A1 | 4/2004 | Maas et al. |
| 2004/0078234 A1 | 4/2004 | Tallal |
| 2004/0093242 A1 | 5/2004 | Cadigan et al. |
| 2004/0107117 A1 | 6/2004 | Denny |
| 2004/0111277 A1 | 6/2004 | Pearson et al. |
| 2004/0111291 A1 | 6/2004 | Dust et al. |
| 2004/0117323 A1 | 6/2004 | Mindala |
| 2004/0148198 A1 | 7/2004 | Kalies |
| 2004/0153336 A1 | 8/2004 | Virdee et al. |
| 2004/0172281 A1 | 9/2004 | Stanners |
| 2004/0172313 A1 | 9/2004 | Stein et al. |
| 2004/0188998 A1 | 9/2004 | Henthorn |
| 2004/0249745 A1 | 12/2004 | Baaren |
| 2005/0015280 A1 | 1/2005 | Gabel et al. |
| 2005/0033604 A1 | 2/2005 | Hogan |
| 2005/0033610 A1 | 2/2005 | Cunningham |
| 2005/0060201 A1 | 3/2005 | Connely, III et al. |
| 2005/0065821 A1 | 3/2005 | Kalies |
| 2005/0086081 A1 | 4/2005 | Brock-Fisher |
| 2005/0090425 A1 | 4/2005 | Reardan et al. |
| 2005/0102169 A1 | 5/2005 | Wilson |
| 2005/0102170 A1* | 5/2005 | Lefever et al. ............... 705/4 |
| 2005/0125292 A1 | 6/2005 | Kassab et al. |
| 2005/0154627 A1 | 7/2005 | Zuzek et al. |
| 2005/0171815 A1 | 8/2005 | Vanderveen |
| 2005/0187793 A1 | 8/2005 | Myles |
| 2005/0197862 A1 | 9/2005 | Paterson et al. |
| 2005/0240473 A1 | 10/2005 | Ayers, Jr. et al. |
| 2005/0288972 A1 | 12/2005 | Marvin et al. |
| 2006/0015518 A1 | 1/2006 | Eletreby et al. |
| 2006/0020514 A1 | 1/2006 | Yered |

| | | | |
|---|---|---|---|
| 2006/0026041 | A1 | 2/2006 | Ullman |
| 2006/0085230 | A1 | 4/2006 | Brill et al. |
| 2006/0149587 | A1 | 7/2006 | Hill, Sr. et al. |
| 2006/0149784 | A1 | 7/2006 | Tholl et al. |
| 2006/0184391 | A1 | 8/2006 | Barre et al. |
| 2006/0224415 | A1 | 10/2006 | Hudson et al. |
| 2006/0229915 | A1 | 10/2006 | Kosinski et al. |
| 2006/0247948 | A1 | 11/2006 | Ellis et al. |
| 2006/0259363 | A1 | 11/2006 | Jhetam et al. |
| 2006/0271398 | A1 | 11/2006 | Belcastro |
| 2006/0271405 | A1 | 11/2006 | Cipolle et al. |
| 2006/0287886 | A1 | 12/2006 | Kitazawa |
| 2007/0005402 | A1 | 1/2007 | Kennedy et al. |
| 2007/0050209 | A1 | 3/2007 | Yered |
| 2007/0050219 | A1* | 3/2007 | Sohr et al. ................... 705/4 |
| 2007/0088567 | A1 | 4/2007 | Berkelhamer et al. |
| 2007/0088576 | A1 | 4/2007 | de Beus et al. |
| 2007/0124177 | A1 | 5/2007 | Engleson et al. |
| 2007/0136100 | A1 | 6/2007 | Daugherty et al. |
| 2007/0179957 | A1 | 8/2007 | Gibson et al. |
| 2007/0233525 | A1 | 10/2007 | Boyle |
| 2007/0233526 | A1 | 10/2007 | Hoffman et al. |
| 2007/0239493 | A1 | 10/2007 | Sweetland et al. |
| 2008/0027759 | A1* | 1/2008 | Flam et al. ................... 705/4 |

FOREIGN PATENT DOCUMENTS

| | | |
|---|---|---|
| EP | 1310895 A2 | 11/2002 |
| WO | 9106917 A1 | 5/1991 |
| WO | 9503569 A3 | 2/1995 |
| WO | 9725682 A1 | 7/1997 |
| WO | 9850871 A1 | 11/1998 |
| WO | 0039737 A1 | 7/2000 |
| WO | 2007025295 A2 | 3/2007 |

OTHER PUBLICATIONS

Sampson, R.J., Taking Control of Health Care Costs, Best's Review—Life Health Insurance Edition, Nov. 1983, pp. 64-66, vol. 84, Issue 7, USA.

Anonymous, ACS to Demonstrate Electronic Health Record Solution Suite at MMIS 2007 Conference; EHR Tools Consolidate Data, Provide Useful Information at the Point of Care for Medicaid Providers, Payers, and Patients, PR Newswire, Aug. 13, 2007, New York, NY, USA.

Lamb, J., New Era of Electronic Medicine Management: E-Prescriptions, Britain's Traditionally Cautious National Health Service is Starting Trials for Online Prescription, with the Aim of Cutting Costs. Financial Times, London, Feb. 21, 2001, p. 6, London, United Kingdom.

Anonymous, Pharmacy Industry Leaders Launch Firm to Supply Real-Time Data. PR Newswire. Jul. 30, 2001, p. 1, New York, NY, USA.

Anonymous, Medic: On-line Goes In-House, Chain Store Age Executive, Jan. 1987, pp. 128-132. vol. 63, Issue 1, USA.

Anonymous, TechRx Announces Successful Beta Deployment of T-Rex. PR Newswire. May 13, 2002.

"Two automatic identification technology, neither new in the sense if being recent developments . . . " Patient Safety & Quality Healthcare [Online] Aug. 2005. URL: http://www.awarix.com.

"Subnotebooks, Phones, and More. St. Vincent's Gets on Track." Mobile Health Data [Online], Nov. 19, 2004. URL: http://www.awarix.com.

"Coping with Information Overload." The News Source for Healthcare Information Technology [Online] Nov. 2004. URL: http://www.awarix.com.

"St. Vincent's first to use Birmingham startup's information system." The Birmingham News [Online] Apr. 11, 2005. URL: http://www.awarix.com.

"St. Vincent's is Digital Flagship" D. Lockridge; Birmingham Medical News [Online] Sep. 2005. URL: http://www.awarix.com.

Non-Final Office Action for U.S. Appl. No. 12/570,953 mailed Nov. 21, 2011.

Non-Final Office Action for U.S. Appl. No. 12/644,232 mailed Dec. 8, 2011.

Non-final Office Action for U.S. App. No. 12/696,677 mailed Dec. 20, 2011.

Final Office Action for U.S. Appl. No. 12/570,953 mailed Mar. 16, 2012.

Final Office Action for U.S. Appl. No. 12/644,232 mailed Mar. 28, 2012.

Final Office Action for U.S. Appl. No. 12/696,677 mailed May 2, 2012.

* cited by examiner

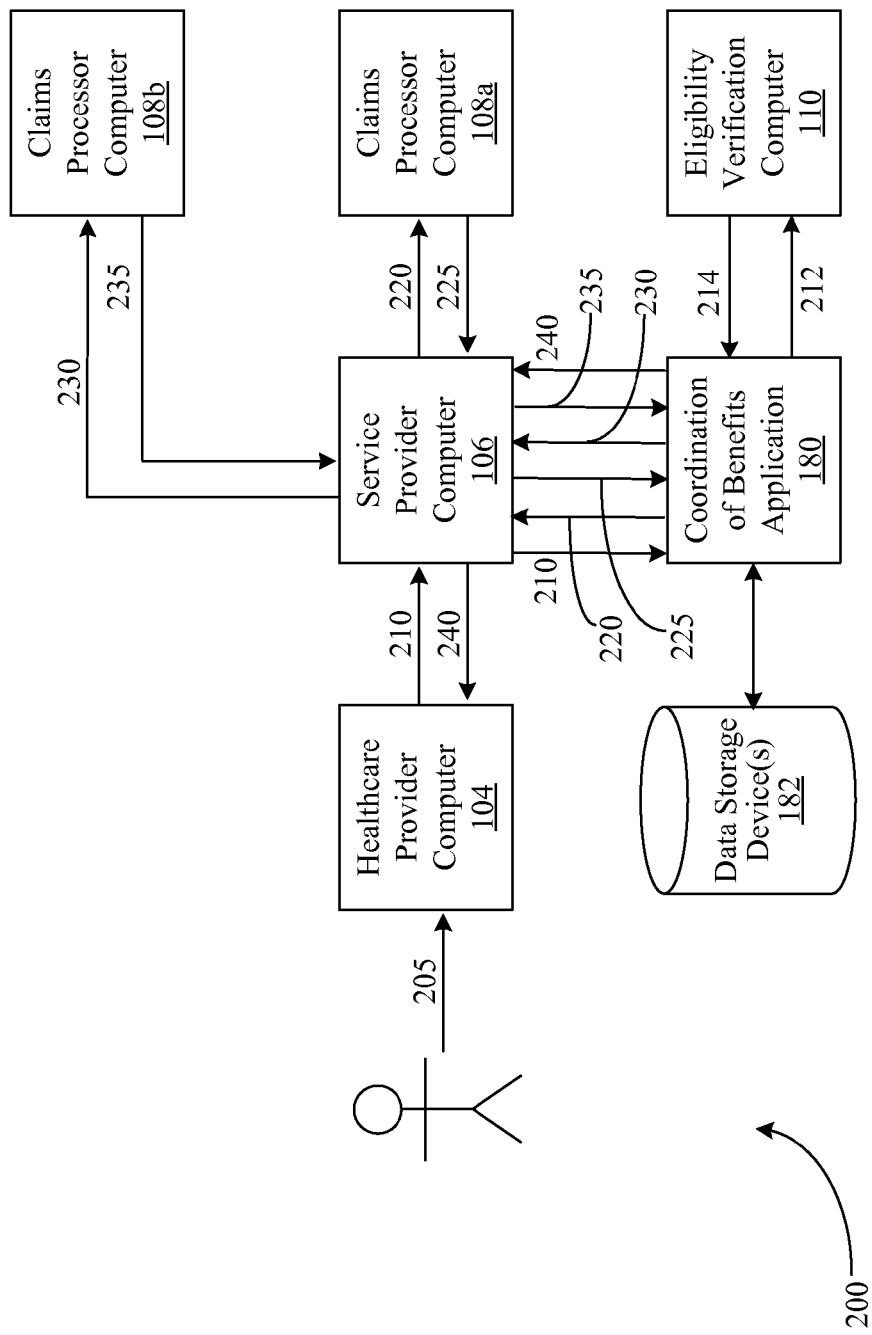

SYSTEMS AND METHODS FOR THE INTELLIGENT COORDINATION OF BENEFITS IN HEALTHCARE TRANSACTIONS

FIELD OF THE INVENTION

Aspects of the invention relate generally to healthcare transactions, and more particularly, to the intelligent coordination of benefits in healthcare transactions.

BACKGROUND OF THE INVENTION

During the processing of a healthcare transaction by a healthcare provider, such as a pharmacy or hospital, a healthcare claim, such as an insurance claim, is typically made by the healthcare provider in order to receive compensation for provided products and/or services. However, in many situations, a patient may have dual prescription coverage and/or multiple benefit payers. For example, a commercial insurance provider may cover all the cost of a medication except for a patient responsibility amount. A state provider, such as a Medicaid provider, may then cover the patient responsibility amount. In dual or multiple coverage situations, a healthcare provider must submit claims to each benefit provider separately and inform providers of amounts that have been paid by previous providers. Such individual claim submissions may be time consuming for the healthcare provider and may be susceptible to inaccuracies as employees of the healthcare provider submit multiple claim requests.

Therefore, a need exists for systems and methods for the intelligent coordination of benefits in healthcare transactions.

BRIEF DESCRIPTION OF THE INVENTION

Some or all of the above needs and/or problems may be addressed by certain embodiments of the invention. Embodiments of the invention may include systems, methods, and apparatus for the intelligent coordination of benefits in healthcare transactions. In one embodiment, a computer-implemented method for the coordination of benefits in healthcare transactions is provided. The method may include receiving a healthcare claim request from a healthcare provider computer, the healthcare claim request including patient information identifying a patient, and product information identifying a product for the patient; determining, based at least in part from a portion of the patient information in the healthcare transaction claim request, that the patient is associated with at least a first payer and a second payer; generating a primary claim request based upon the identified product and the patient associated with the healthcare claim request, the primary claim associated with the first payer; communicating the generated primary claim request to a first claims processor computer associated with the first payer for adjudication; receiving, from the first claims processor computer, a first adjudicated reply for the primary claim, the first adjudicated reply indicating first financial coverage information for the identified product for the patient; generating a coordination of benefits (COB) claim request based at least in part on the received first adjudicated reply, the COB claim request including at least a portion of the first financial coverage information for the identified product, the COB claim request associated with a second payer; communicating the generated COB claim request to a second claims processor computer associated with the second payer for adjudication; receiving, from the second claims processor computer, a second adjudicated reply for the COB claim; and communicating information associated with the first adjudicated reply and the second adjudicated reply to the healthcare provider computer. It will be appreciated that the above operations may be performed by one or more computers associated with a service provider.

In accordance with another embodiment of the invention, a system for the intelligent coordination of benefits in healthcare transactions is provided. The system may include at least one memory and at least one processor. The at least one memory may be operable to store computer-executable instructions. The at least one processor may be configured to access the at least one memory and execute the computer-executable instructions to: receive a healthcare claim request from a healthcare provider computer, the healthcare claim request including patient information identifying a patient, and product information identifying a product for the patient; determine, based at least in part from a portion of the patient information in the healthcare transaction claim request, that the patient is associated with at least a first payer and a second payer; generate a primary claim request based upon the identified product and the patient associated with the healthcare claim request, the primary claim associated with the first payer; communicate the generated primary claim request to a first claims processor computer associated with the first payer for adjudication; receive, from the first claims processor computer, a first adjudicated reply for the primary claim, the first adjudicated reply indicating first financial coverage information for the identified product for the patient; generate a coordination of benefits (COB) claim request based at least in part on the received first adjudicated reply, the COB claim request including at least a portion of the first financial coverage information for the identified product, the COB claim request associated with a second payer; communicate the generated COB claim request to a second claims processor computer associated with the second payer for adjudication; receive, from the second claims processor computer, a second adjudicated reply for the COB claim; and communicate information associated with the first adjudicated reply and the second adjudicated reply to the healthcare provider computer.

Additional systems, methods, apparatus, features, and aspects may be realized through the techniques of various embodiments of the invention. Other embodiments and aspects of the invention are described in detail herein with reference to the description and to the drawings and are considered a part of the claimed invention.

BRIEF DESCRIPTION OF THE DRAWINGS

Reference will now be made to the accompanying drawings, which are not necessarily drawn to scale, and wherein:

FIGS. 2A and 2B provide example diagrams for coordinating benefits in healthcare transactions that are processed through a service provider, according to an example embodiment of the invention.

DETAILED DESCRIPTION

Embodiments of the invention now will be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Embodiments of the invention can provide systems, methods, apparatus, means, and/or mechanisms for the intelligent coordination of benefits in healthcare transactions. In this regard, a service provider computer may receive a single healthcare transaction request for a patient from a healthcare provider computer. The service provider computer, either alone or in conjunction with another computer or entity (e.g., eligibility verification computer), may automatically determine whether the patient is associated with one or more payers. The service provider computer may automatically generate one or more healthcare claim requests as needed or as available, which are delivered to the appropriate claims processor computers associated with the payers for adjudication. The service provider computer may coordinate the generation and delivery of the healthcare claim requests, and may receive replies in response to the adjudicated requests. A single response may be provided from the service provider computer to the healthcare provider computer, where the single response may include information from the received replies in response to the adjudicated requests.

System Overview

Figure 1:
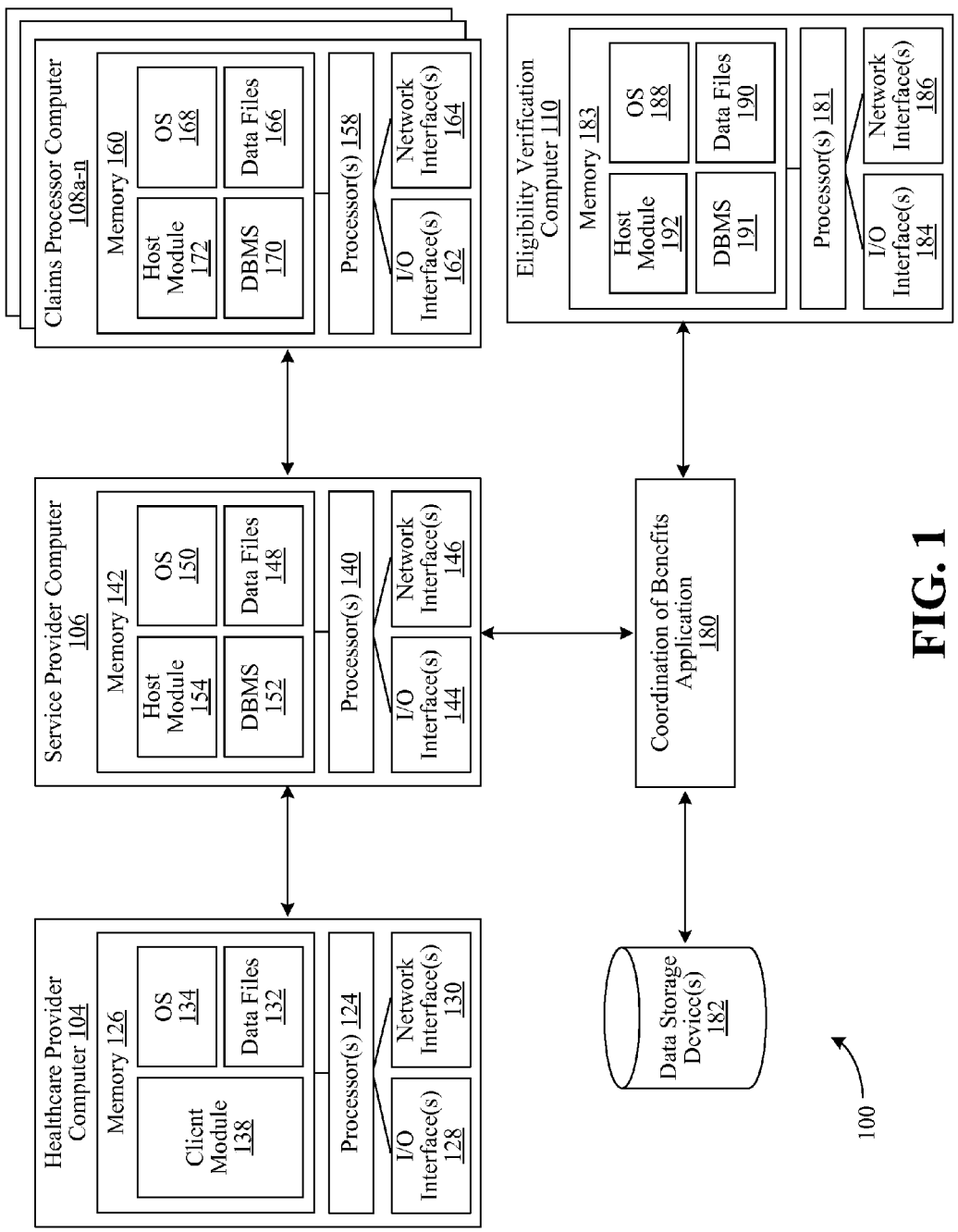
FIG. 1 illustrates an example overview of a system that facilitates the intelligent coordination of benefits in healthcare transactions, according to an example embodiment of the invention.

An example system 100 for facilitating the intelligent coordination of benefits in healthcare transactions will now be described illustratively with respect to FIG. 1. As shown in FIG. 1, the system 100 may include one or more healthcare provider computers 104, service provider computers 106, claims processor computers 108*a-n*, and eligibility verification computers 110. As desired, each of the healthcare provider computer 104, service provider computer 106, claims processor computers 108*a-n*, and eligibility verification computer 110 may include one or more processing devices that may be configured for accessing and reading associated computer-readable media having stored thereon data and/or computer-executable instructions for implementing the various methods of the invention.

Additionally, in certain embodiments, the service provider computer 106 may include or otherwise be in communication with a coordination of benefits (COB) application 180 or COB module, which may facilitate the determination that multiple payers are available or associated with the patient. For example, the COB application 180 may receive a healthcare transaction request originating from a healthcare provider computer 104. The healthcare transaction request may include information identifying at least a patient, and a product (e.g., drug, medication, or other medical product) for the patient. The COB application 180 may determine, based at least in part on the patient identification information of the received healthcare transaction request, that two or more payers are available or associated with the patient. Thus, the COB application 180 may coordinate the generation and/or processing of a primary claim request and one or more coordination of benefits (COB) claim requests for the requested product for the patient. For example, the COB application 180 may additionally analyze information included in adjudicated replies that are received from one or more claims processor computers 108*a-n*, and utilize that information in the generation of claims requests, such as COB claim requests. Additionally, as desired, the COB application 180 may generate or assemble a single adjudicated reply for the healthcare transaction request and direct the communication of the single adjudicated reply to the healthcare provider computer 104 that originated the healthcare transaction request.

Generally, network devices and systems, including one or more of the healthcare provider computer 104, service provider computer 106, claims processor computers 108*a-n*, and eligibility verification computer 110 may include or otherwise be associated with suitable hardware and/or software for transmitting and receiving data and/or computer-executable instructions over one or more communications links or networks. These network devices and systems may also include any number of processors for processing data and executing computer-executable instructions, as well as other internal and peripheral components that are well-known in the art. Further, these network devices and systems may include or be in communication with any number of suitable memory devices operable to store data and/or computer-executable instructions. By executing computer-executable instructions, each of the network devices may form a special purpose computer or particular machine. As used herein, the term "computer-readable medium" describes any form of suitable memory or memory device.

The healthcare provider computer 104 may be associated with a healthcare provider, for example, a pharmacy, physician's office, hospital, etc. The healthcare provider computer 104 may be any suitable processor-driven device that facilitates the processing of healthcare requests (e.g., prescription orders) made by or on behalf of patients or consumers and the communication of information associated with healthcare transaction requests (e.g., healthcare claim transactions, healthcare claim requests, eligibility transaction requests, etc.) to the service provider computer 106. For example, the healthcare provider computer 104 may be a computing device that includes any number of server computers, mainframe computers, networked computers, desktop computers, personal computers, digital assistants, personal digital assistants, digital tablets, Internet appliances, application specific circuits, microcontrollers, minicomputers, and/or any other processor-based device(s). In certain embodiments, the healthcare provider computer 104 may be a suitable point of sale device associated with a healthcare provider. The execution of the computer-implemented instructions by the healthcare provider computer 104 may form a special purpose computer or other particular machine that is operable to facilitate the processing of healthcare requests (e.g., prescription orders) made by or on behalf of patients and the communication of information associated with healthcare transaction requests (e.g., claim requests and/or healthcare claim transactions, eligibility transaction requests, etc.) to a service provider computer 106. Additionally, in certain embodiments of the invention, the operations and/or control of the healthcare provider computer 104 may be distributed amongst several processing components.

In addition to having one or more processors 124, the healthcare provider computer 104 may include one or more memory devices 126, one or more input/output ("I/O") interface(s) 128, and one or more network interface(s) 130. The memory devices 126 may be any suitable memory device, for example, caches, read only memory devices, random access memory devices, magnetic storage devices, removable storage devices, etc. The memory devices 126 may store data, executable instructions, and/or various program modules utilized by the healthcare provider computer 104, for example, data files 132, an operating system 134, and/or a client module 138. The data files 132 may include any suitable data that facilitates the receipt and/or processing of healthcare requests (e.g., prescription orders) by the healthcare provider computer 104 and the generation and/or processing of healthcare transaction requests (e.g., healthcare claim requests, healthcare claim transactions, eligibility transaction requests, etc.) that are communicated to the service provider computer 106. For example, the data files 132 may include, but are not limited to, healthcare information associated with one or more patients, information associated with the service provider computer 106, information associated with one or more claims processors, information associated with one or more healthcare transaction requests, and/or information associated with the generation of healthcare claim requests. The operating system (OS) 134 may be a suitable software module that controls the general operation of the healthcare provider computer 104. The OS 134 may also facilitate the execution of other software modules by the one or more processors 124, for example, the client module 138. The OS 134 may be, but is not limited to, Microsoft Windows®, Apple OSX™, Linux, Unix, or a mainframe operating system. The client module 138 may be an Internet browser or other software, including a dedicated program, for interacting with the service provider computer 106. For example, a user such as a pharmacist or other pharmacy employee, may utilize the client module 138 in preparing and providing a prescription claim request to the service provider computer 106 for delivery to one or more appropriate claims processor computers 108, for adjudication or other coverage/benefits determination. The healthcare provider computer 104 may also utilize the client module 138 to retrieve or otherwise receive data, messages, or responses from the service provider computer 106 and/or other components of the system 100.

In operation, the healthcare provider computer 104 may receive information associated with a healthcare request (e.g., prescription order) from a patient. As one example, the healthcare provider computer 104 may receive information associated with a healthcare request for a patient at a point of sale, such as in a pharmacy during a prescription fulfillment or purchase transaction. As another example, the healthcare provider computer 104 may electronically receive a healthcare request from a physician computer, a patient computer, or other patient device. The healthcare provider computer 104 may generate a healthcare transaction request (e.g., healthcare claim request, healthcare claim transaction, eligibility transaction request, etc.), and information associated with the healthcare transaction request may be communicated to the service provider computer 106.

The one or more I/O interfaces 128 may facilitate communication between the healthcare provider computer 104 and one or more input/output devices, for example, one or more user interface devices, such as, a display, keypad, control panel, touch screen display, remote control, microphone, etc. that facilitate user interaction with the healthcare provider computer 104. For example, the one or more I/O interfaces 128 may facilitate entry of information associated with a healthcare transaction request (e.g., healthcare claim transaction, healthcare claim request, eligibility transaction request, etc.) by an employee of a healthcare provider, such as a pharmacy employee. The one or more network interfaces 130 may facilitate connection of the healthcare provider computer 104 to one or more suitable networks, for example, a local area network, a wide area network, the Internet, a cellular network, a publicly switched telephone network, a dedicated healthcare transactions network, any wired network, any wireless network, a combination of networks, etc. In this regard, the healthcare provider computer 104 may receive and/or communicate information to other network components of the system 100, such as the service provider computer 106.

With continued reference to FIG. 1, the service provider computer 106 may include, but is not limited to, any suitable processor-driven device that is configured for receiving, processing, and fulfilling requests from the healthcare provider computer 104 and/or claims processor computers 108a-n relating to prescription, pharmacy, benefits, eligibility, and/or healthcare transactions and/or other activities. In certain embodiments, the service provider computer 106 may be a switch/router that routes healthcare transactions comprising requests and replies/responses. For example, the service provider computer 106 may route billing requests and/or prescription claim requests communicated from the healthcare provider computer 104 to one or more claims processor computers 108a-n, which may be associated with pharmacy benefits managers (PBM), insurers, government payers, or claims clearinghouses. In certain embodiments, the service provider computer 106 may include a suitable host server, host module, or other software that facilitates the receipt of a healthcare transaction request from a healthcare provider computer 104 and/or the routing of claim requests to various claims processor computers 108a-n.

The service provider computer 106 may include any number of special purpose computers or other particular machines, application specific circuits, microcontrollers, personal computers, minicomputers, mainframe computers, servers, networked computers, and/or other processor-driven devices. In certain embodiments, the operations of the service provider computer 106 may be controlled by computer-executed or computer-implemented instructions that are executed by one or more processors associated with the service provider computer 106 to form a special purpose computer or other particular machine that is operable to facilitate the receipt, routing, and/or processing of healthcare claim requests or healthcare claim transactions. The one or more processors that control the operations of the service provider computer 106 may be incorporated into the service provider computer 106 and/or may be in communication with the service provider computer 106 via one or more suitable networks. In certain embodiments of the invention, the operations and/or control of the service provider computer 106 may be distributed amongst several processing components.

Similar to the healthcare provider computer 104, the service provider computer 106 may include one or more processors 140, one or more memory devices 142, one or more input/output ("I/O") interface(s) 144, and one or more network interfaces 146. The one or more memory devices 142 may be any suitable memory devices, for example, caches, read only memory devices, random access memory devices, magnetic storage devices, removable memory devices, etc. The one or more memory devices 142 may store data, executable instructions, and/or various program modules utilized by the service provider computer 106, for example, data files 148, an operating system ("OS") 150, the host module 154, and a database management system ("DBMS") 152 to facilitate management of data files 148 and other data stored in the memory devices 142 and/or one or more databases or data storage devices 182. The OS 150 may be, but is not limited to, Microsoft Windows®, Apple OSX™, Linux, Unix, or a mainframe operating system.

According to an embodiment of the invention, the data files 148 may store healthcare transaction records associated with communications received from various healthcare provider computers 104 and/or various claims processor computers 108a-n. The data files 148 may also store any number of suitable routing tables that facilitate determining the destination of communications received from a healthcare provider computer 104 or claims processor computer 108a-n and/or the destination of claims generated by the COB application 180. The host module 154 may receive, process, and respond to requests from the client module 138 of the healthcare provider computer 104, and may further receive, process, and respond to requests of the respective host modules 172 of the various claims processor computers 108a-n. The service provider computer 106 may include additional program modules for performing other processing methods described herein. Those of ordinary skill in the art will appreciate that the service provider computer 106 may include alternate and/or additional components, hardware or software without departing from example embodiments of the invention.

A coordination of benefits (COB) application 180 or COB module may also be operative with the service provider computer 106. The COB application 180 may include computer-executable instructions for identifying or otherwise determining whether multiple payers are associated with the patient. For example, the COB application 180 may receive a healthcare transaction request originating from a healthcare provider computer 104. The healthcare transaction request may include information identifying at least a patient, and a product (e.g., drug, medication, or other medical product) for the patient. The COB application 180 may determine, based at least in part on the patient identification information of the received healthcare transaction request, that two or more payers are available or associated with the patient. Thus, the COB application 180 may coordinate the generation and/or processing of a primary claim request and one or more coordination of benefits (COB) claim requests for the requested product for the patient.

More particularly, if the COB application 180 identifies that multiple payers are available, then the COB application 180 may determine a priority among the identified payers. This priority may determine an order or sequence in which healthcare claim requests are generated and routed to the respective identified payers. As an example, a private payer of the identified payers may be identified as a first payer that would receive and adjudicate a first or primary healthcare claim request. Likewise, a government payer of the identified payers may be identified as a payer of last resort that would receive and adjudicate a last COB claim request, if necessary (e.g., as requested or if any amounts remain unpaid by preceding payers, including the first payer).

Once the priority among the identified payers has been determined, the COB application 180 may then generate and coordinate the communication of claim requests to a plurality of payers for adjudication. For example, the COB application 180 may generate a primary claim request and direct the service provider computer 106 to route or otherwise communicate the primary claim request to a first claims processor computer 108a associated with a first payer. A first adjudicated reply for the primary claim request may then be received by the service provider computer 106 from the first claims processor computer 108a, and the first adjudicated reply, a copy of the reply, or information included in the reply may be communicated to the COB application 180. The COB application 180 may then generate a COB claim request based at least in part on the information included in the first adjudicated reply, and the COB application 180 may direct the service provider computer 106 to route or otherwise communicate the COB claim request to a second claims processor computer 108b associated with the COB request. A second adjudicated reply for the COB claim request may then be received by the service provider computer 106 from the second claims processor computer 108b, and the second adjudicated reply, a copy of the reply, or information included in the reply may be communicated to the COB application 180. As desired, the COB application 180 may generate additional COB claim requests in an iterative manner based upon the received adjudicated replies. The COB application 180 may continue to generate and/or route claim requests to additional claims processor computers 108n associated with the additional payers until all relevant claims are fully paid or until no more payers are available. Once processing by the COB application 180 is complete, the COB application 180 may generate or construct a single reply/response to the healthcare transaction request based upon each of the received adjudicated replies, and the COB application 180 may direct the service provider computer 106 to route the single reply/response to the healthcare provider computer 104. As an alternative to generating a single reply/response, each of the received adjudicated replies may be communicated to the healthcare provider computer 104.

In certain embodiments of the invention, the COB application 180 may construct a COB claim request based upon information included in received adjudicated replies for one or more previous claim requests. In this regard, a requested claim amount or payment amount included in a COB claim request may be based upon one or more payments that have been made or approved in conjunction with previously adjudicated claim requests for the healthcare transaction. For example, a primary claim request may be generated for a prescription medication and communicated to an appropriate claims processor computer 108a associated with an insurance provider or PBM. An adjudicated reply received for the primary claim request may indicate that all of the medication cost will be covered other than a patient responsibility amount (e.g., a co-insurance or co-pay amount, such as twenty dollars ($20). A COB claim request for the patient responsibility amount (e.g., twenty dollars) may be generated for the prescription medication and communicated to an appropriate claims processor computer 110b associated with a government payer (e.g., Medicaid or Medicare) to request payment of the patient responsibility amount. Once an adjudicated reply is received for the COB claim request, a single reply may be generated or built for communication to the healthcare provider computer 104.

As desired in various embodiments, if a claim request is denied by a claims processor computer 108a-n or if an expected payment amount is not made or authorized, then information included in the claim request may be utilized to generate a second claim request. For example, if a primary claim request is denied, then a COB claim request (or another primary claim request) may be generated using the primary claim request data or information. The COB claim request (or primary claim request) may then be communicated to an appropriate claims processor computer 108a-n for adjudication. This process may be repeated as desired until the claim is paid or until no other payers are available for the healthcare transaction. In this regard, if a first payer does not authorize payment for a claim, then a claim request may be sent to a second payer, third payer, and so on. For example, if a patient has two insurance providers and a first of the insurance providers denies a claim, then a claim request may be communicated to the second insurance provider in an attempt to have the claim approved. If the claim is ultimately approved, then one or more additional COB claim requests may be generated as desired in the event that other payers/claims processor computers are available. An example of operations for generating claim requests based upon the adjudicated replies received for one or more previous requests is provided below with reference to FIGS. 2-4.

The data storage devices 182 (e.g., databases) may be accessible by the COB application 180, and the data storage devices 182 be operable to store healthcare claim transaction information, such as information that may be utilized by the COB application 180 to construct one or more claim requests and/or information (e.g., adjudicated replies) that may be utilized to generate or build a response/reply for a healthcare claim request.

With continued reference to the service provider computer 106, the one or more I/O interfaces 144 may facilitate communication between the service provider computer 106 and one or more input/output devices, for example, one or more user interface devices, such as, a display, keypad, control panel, touch screen display, remote control, microphone, etc. that facilitate user interaction with the service provider computer 106. The one or more network interfaces 146 may facilitate connection of the service provider computer 106 to one or more suitable networks, for example, a local area network, a wide area network, the Internet, a cellular network, a publicly switched telephone network, a dedicated healthcare transactions network, any wired network, any wireless network, a combination of networks, etc. In this regard, the service provider computer 106 may communicate with other components of the system 100.

With continued reference to FIG. 1, any number of claims processor computers 108a-n may be provided. Each claims processor computer 108a-n may be any suitable processor-driven device that facilitates receiving, processing, and/or fulfilling healthcare claim transactions and/or healthcare claim requests received from the service provider computer 106. For example, a claims processor computer 108a-n may be a processor-driven device associated with a pharmacy benefits manager (PBM), an insurer, a government payer, or a claims clearinghouse. As desired, the claims processor computer 108 may include any number of special purpose computers or other particular machines, application specific circuits, microcontrollers, personal computers, minicomputers, mainframe computers, servers, and the like. In certain embodiments, the operations of a claims processor computer 108a-n may be controlled by computer-executed or computer-implemented instructions that are executed by one or more processors associated with the claims processor computer 108a-n to form a special purpose computer or other particular machine that is operable to facilitate the receipt, processing, and/or fulfillment of healthcare claim transaction requests received from the service provider computer 106. The one or more processors that control the operations of the claims processor computer 108a-n may be incorporated into the claims processor computer 108a-n and/or in communication with the claims processor computer 108a-n via one or more suitable networks. In certain embodiments of the invention, the operations and/or control of the claims processor computer 108a-n may be distributed amongst several processing components.

Similar to other components of the system 100, each claims processor computer 108a-n may include one or more processors 158, one or more memory devices 160, one or more input/output ("I/O") interface(s) 162, and one or more network interfaces 164. The one or more memory devices 160 may be any suitable memory devices, for example, caches, read only memory devices, random access memory devices, magnetic storage devices, removable memory devices, etc. The one or more memory devices 160 may store data, executable instructions, and/or various program modules utilized by the claims processor computer 108a-n, for example, data files 166, an operating system ("OS") 168, a database management system ("DBMS") 170, and a host module 172. The data files 166 may include any suitable information that is utilized by the claims processor computer 108 to process healthcare claim transactions, for example, patient profiles, patient insurance information, other information associated with a patient, information associated with a healthcare provider, etc. The operating system (OS) 168 may be a suitable software module that controls the general operation of the claims processor computer 108. The OS 168 may also facilitate the execution of other software modules by the one or more processors 158, for example, the DBMS 170 and/or the host module 172. The OS 168 may be, but is not limited to, Microsoft Windows®, Apple OSX™, Linux, Unix, or a mainframe operating system. The DBMS 170 may be a suitable software module that facilitates access and management of one or more databases that are utilized to store information that is utilized by the claims processor computer 108 in various embodiments of the invention. The host module 172 may initiate, receive, process, and/or respond to requests, such as healthcare claim transactions or claim requests, from the host module 154 of the service provider computer 106. The claims processor computer 108 may include additional program modules for performing other pre-processing or post-processing methods described herein. Those of ordinary skill in the art will appreciate that the claims processor computer 108 may include alternate and/or additional components, hardware or software without departing from example embodiments of the invention.

The one or more I/O interfaces 162 may facilitate communication between the claims processor computer 108 and one or more input/output devices, for example, one or more user interface devices, such as a display, keypad, control panel, touch screen display, remote control, microphone, etc. that facilitate user interaction with the claims processor computer 108. The one or more network interfaces 164 may facilitate connection of the claims processor computer 108 to one or more suitable networks, for example, a local area network, a wide area network, the Internet, a cellular network, a publicly switched telephone network, a dedicated healthcare transactions network, any wired network, any wireless network, a combination of networks, etc. In this regard, the claims processor computer 108 may receive healthcare claim transactions and/or other communications from the service provider computer 106, and the claims processor computer 108 may communicate information associated with processing claim transactions to the service provider.

With continued reference to FIG. 1, one or more eligibility verification computers 110 may be provided. The eligibility verification computer 110 may be any suitable processor-driven device that may determine whether one or more payers are available for one or more patients. In this regard, the eligibility verification computer 110 may receive eligibility verification requests for one or more patients, and respond with information regarding any payers available for the one or more patients. For example, the eligibility verification computer may be a processor-driven device associated with an eligibility service provider, a data management provider, or one or more payers. As desired, the eligibility verification computer 110 may include any number of special purpose computers or other particular machines, application specific circuits, microcontrollers, personal computers, minicomputers, mainframe computers, servers, and the like. In certain embodiments, the operations of the eligibility verification computer 110 may be controlled by computer-executed or computer-implemented instructions that are executed by one or more processors associated with the eligibility verification computer 110 to form a special purpose computer or other particular machine that is operable to facilitate the receipt and processing of eligibility requests received from the service provider computer 106 or another computer. The one or more processors that control the operations of the eligibility verification computer 110 may be incorporated into the eligibility verification computer 110 and/or in communication with the eligibility verification computer 110 via one or more suitable networks. In certain embodiments of the invention, the operations and/or control of the eligibility verification computer 110 may be distributed amongst several processing components.

Similar to other components of the system 100, the eligibility verification computer 110 may include one or more processors 181, one or more memory devices 183, one or more I/O interfaces 184, and/or one or more network interfaces 186. The one or more memory devices 183 may be any suitable memory devices, for example, caches, read only memory devices, random access memory devices, magnetic storage devices, removable memory devices, etc. The one or more memory devices 183 may store data, executable instructions, and/or various program modules utilized by the eligibility verification computer 110, for example, data files 190, an operating system ("OS") 188, a database management system ("DBMS") 191, and a host module 192. The data files 190 may include any suitable information that is utilized by the eligibility verification computer 110 to process eligibility verification requests, for example, patient profiles, patient insurance information, payer information, other information associated with a patient, information associated with a healthcare provider, etc. In addition, the data files 190 may aggregate payer information for each patient such that a plurality of payers may be identified for each patient. It will be appreciated that the same or similar information as provided by the data files 190 could likewise be stored in a data storage device 182, as described herein. Likewise, in some example embodiments of the invention, the eligibility verification computer 110 could likewise be implemented as part of the service provider computer 106 and/or the coordination of benefits (COB) application 180 without departing from example embodiments of the invention. In yet another alternative embodiment of the invention, the eligibility verification computer 110 could also be implemented as part of an another entity or processor that is designed to receive and respond to eligibility requests.

Still referring to the eligibility verification computer 110, the operating system (OS) 188 may be a suitable software module that controls the general operation of the eligibility verification computer 110. The OS 188 may also facilitate the execution of other software modules by the one or more processors 181, for example, the DBMS 191 and/or the host module 192. The OS 188 may be, but is not limited to, Microsoft Windows®, Apple OSX™, Linux, Unix, or a mainframe operating system. The DBMS 191 may be a suitable software module that facilitates access and management of one or more databases that are utilized to store information that is utilized by the eligibility verification computer 110 in various embodiments of the invention. The host module 192 may initiate, receive, process, and/or respond to requests, such as eligibility verification requests, from the host module 154 of the service provider computer 106 or the coordination of benefits application 180. The eligibility verification computer 110 may include additional program modules for performing other pre-processing or post-processing methods described herein. Those of ordinary skill in the art will appreciate that the eligibility verification computer 110 may include alternate and/or additional components, hardware or software without departing from example embodiments of the invention.

Any number of networks may be utilized in association with various embodiments of the invention to facilitate communications between any number of components of the system. The network(s) may also allow for real-time, off-line, and/or batch transactions to be transmitted between or among the healthcare provider computer 104, the service provider computer 106, the claims processor computers 108a-n, and the eligibility verification computer 110. Due to network connectivity, various methodologies as described herein may be practiced in the context of distributed computing environments. A wide variety of network configurations may be utilized as desired in various embodiments of the invention. Instead of, or in addition to, a network or combination of networks, dedicated communication links may be used to connect the various devices in accordance with an example embodiment of the invention. For example, the service provider computer 106 may form the basis of a network that interconnects the healthcare provider computer 104 and one or more claims processor computers 108 and the eligibility verification computer 110.

Those of ordinary skill in the art will appreciate that the system 100 shown in and described with respect to FIG. 1 is provided by way of example only. Numerous other operating environments, system architectures, and device configurations are possible. Other system embodiments can include fewer or greater numbers of components and may incorporate some or all of the functionality described with respect to the system components shown in FIG. 1. For example, in one embodiment, the service provider computer 106 (or other computer) may be implemented as a specialized processing machine that includes hardware and/or software for performing the methods described herein. In addition, at least a portion of the processor and/or processing capabilities of the service provider computer 106 and/or the COB application 180, may be implemented as part of a claims processor computer, such as the first claims processor computer 108a. Accordingly, embodiments of the invention should not be construed as being limited to any particular operating environment, system architecture, or device configuration.

Operational Overview

FIG. 2A is an example block diagram 200 for coordinating benefits in healthcare transactions that are processed through a service provider, such as the service provider computer 106 illustrated in FIG. 1. With reference to FIG. 2A, a healthcare provider computer, such as the healthcare provider computer 104 illustrated in FIG. 1, may receive a healthcare request 205 from a patient. The healthcare request 205 may be a prescription order that is received in-person or electronically as desired in various embodiments of the invention. For example, a patient may seek to fill a prescription for one or more drugs, medications, and/or other products at a pharmacy location or store. As another example, a patient may communicate a healthcare request 205, such as a request to fill a prescription, to a healthcare provider computer 104 via one or more suitable network connections. For example, a purchase request may be communicated to a healthcare provider computer 104 from a customer computer via a web portal hosted by the healthcare provider computer 104. In addition, a physician/clinic/hospital computer can also communicate a healthcare request 205 as an electronic prescription order (e.g., an E-SCRIPT) to the healthcare provider computer 104.

The healthcare provider computer 104 may receive and process the request 205 to generate a healthcare transaction request 210, which may be in the form of a prescription claim request or an eligibility verification request. The generated healthcare transaction request 210 may be communicated by the healthcare provider computer 104 to the service provider computer 106. Accordingly, the healthcare transaction request 210 may be received by the service provider computer 106.

According to an example embodiment of the invention, the healthcare transaction request 210 may be in accordance with a version of a National Council for Prescription Drug Programs (NCPDP) Telecommunication Standard, although other standards may be utilized as well. As desired, the healthcare transaction request 210 may include a BIN Number and/or Processor Control Number (PCN) for identifying a claims processor computer, such as one of the claims processor computers 108a-n illustrated in FIG. 1, as a destination of the healthcare transaction request 210. In addition, the healthcare transaction request 210 may also include information relating to the patient, payer, prescriber, healthcare provider, and/or the prescribed drug or product. As an example, the healthcare transaction request 210 received by the service provider computer 106 may include one or more of the following information:
    Payer ID/Routing Information for each identified payer or potential payer
        BIN Number and Processor Control Number (PCN) that designates an intended destination of the healthcare transaction request 210
    Patient Information
    Name (e.g., Patient Last Name, Patient First Name, etc.)
    Date of Birth of Patient
    Age of Patient
    Gender
    Patient Address (e.g., Street Address, Zip Code, etc.)
    Patient Contact Information (e.g., Patient Telephone Number)
    Patient ID or other identifier
    Insurance/Coverage Information
    Cardholder Name (e.g., Cardholder First Name, Cardholder Last Name)
    Cardholder ID and/or other identifier (e.g., person code)
    Provider (e.g., Prescriber, Pharmacy) Information
    Prescriber Information
    Primary Care Provider ID or other identifier (e.g., National Provider Identifier (NPI) code)
    Primary Care Provider Name (e.g., Last Name, First Name)
    Prescriber ID or other identifier (e.g., NPI code, DEA number)
    Prescriber Name (e.g., Last Name, First Name)
    Prescriber Contact Information (e.g., Telephone Number)
    Pharmacy or other Healthcare Provider Information (e.g., store name, chain identifier, etc.)
    Pharmacy or other Healthcare Provider ID (e.g., NPI code)
    Claim Information
    Drug or product information (e.g., National Drug Code (NDC))
    Prescription/Service Reference Number
    Date Prescription Written
    Quantity Dispensed
    Number of Days Supply
    Diagnosis/Condition
    Pricing information for the drug or product (e.g., network price, Usual & Customary price)
    Date of Service.

In addition, a healthcare transaction request 210 that is in the form of a prescription claim request can optionally include an appropriate identifier for indicating that eligibility verification of additional payers is additionally requested. A wide variety of identifiers may be utilized as desired in various embodiments of the invention, for example, a certain value (e.g., a value of nine) in an other coverage code (OCC) field for the healthcare transaction request 210.

According to an alternative embodiment of the invention, it will be appreciated that the healthcare transaction request 210 may not necessarily be in the form of a standard prescription claim request, according to an example embodiment of the invention. Instead, the healthcare transaction request 210 may be in the form of an eligibility verification request. An eligibility verification request may include enough information to determine, perhaps in conjunction with the eligibility verification computer 110 or similar eligibility information stored in data storage device 182 or elsewhere, whether a patient is associated with one or more payers. An example eligibility verification request may include one or more of the following information:
    Patient Information
    Name (e.g., Patient Last Name, Patient First Name, etc.)
    Date of Birth of Patient
    Age of Patient
    Gender
    Patient Address (e.g., Street Address, Zip Code, etc.)
    Patient Contact Information (e.g., Patient Telephone Number)
    Patient ID or other identifier
    Claim Information
    Drug or product information (e.g., National Drug Code (NDC))
    Prescription/Service Reference Number
    Date Prescription Written
    Quantity Dispensed
    Number of Days Supply
    Diagnosis/Condition
    Pricing information for the drug or product (e.g., network price, Usual & Customary price)

The eligibility verification request could also include an appropriate identifier (e.g., a specially designated BIN/PCN) to identify that the request is for eligibility verification. In addition, the eligibility verification request could also optionally identify one or more payers, perhaps by respective name, BIN/PCN, or other Payer ID. If the eligibility verification request identifies one or more payers, then respective insurance/coverage information can optionally be included, such as Cardholder Name, Cardholder ID. Likewise, if the eligibility verification request includes more than one payer, then the eligibility verification request can optionally identify a priority or ordering among the payers. The priority or ordering may be used to determine an order in which a primary claim request and corresponding COB claim request(s) are generated and processed, as described herein.

The service provider computer 106 may receive the healthcare transaction request 210 from the healthcare provider computer 104, and the service provider computer 106 and/or an associated COB application, such as the COB application 180 shown in FIG. 1, may process the healthcare transaction request 210. As desired, the service provider computer 106 and/or the COB application 180 may perform one or more pre-edits on the healthcare transaction request 210. For example, the healthcare transaction request 210 may be identified as being an eligibility verification request based upon the recognition of an appropriate identifier, or otherwise requesting eligibility verification of additional payers. Once the healthcare transaction request 210 is identified as being an eligibility verification request or otherwise requesting eligibility verification, the healthcare transaction request 210, a copy of the transaction 210, or information associated with the transaction 210 may be communicated to the COB application 180 for processing. Alternatively, for healthcare transaction requests 210 that are prescription claim requests, the healthcare transaction request 210, a copy of the transaction 210, or information associated with the transaction 210 may be communicated to the COB application 180 for processing based upon preferences set by the pharmacy, patient, service provider, or other healthcare provider.

The COB application 180 may utilize at least the patient information from the healthcare transaction request 210 to determine whether the patient is associated with one or more payers. In an example embodiment of the invention, the COB application 180 may generate an eligibility verification request 212 having at least the patient information from the healthcare transaction request 210. The COB application 180 may deliver the eligibility verification request 212 to the eligibility verification computer 110. The eligibility verification request 212 may be in accordance with an NCPDP format (e.g., an E1 transaction) or X12 format (e.g., a 270 transaction), although other formats or protocols could equally be utilized. The eligibility verification computer 110 may receive the eligibility verification request 212, which includes at least some of the patient information. Using the patient information, for example, a combination of the patient name, date of birth (DOB), zip code, and Cardholder ID, the eligibility verification computer 110 can determine whether the patient is associated with one or more payers. For example, the eligibility verification computer 110 may have access to payer information for a plurality of patients, and may identify one or more payers for a patient by matching according to certain patient information. If the eligibility verification computer 110 identifies one or more payers, then the eligibility verification computer 110 may provide an eligibility response 214 that identifies the one or more payers. For example, the one or more payers may be identified in the eligibility response 214 according to one or both of a respective name or a BIN/PCN number. The eligibility response 214 may also identify a priority, ordering, or ranking among the payers if more than two payers are identified. The priority, ordering, or ranking may be used to determine an order in which claim requests are generated and processed by the two or more identified payers. On the other hand, if the eligibility verification computer 110 cannot identify any payers associated with the patient, then the eligibility response 214 may reflect that no payers have been identified for the patient.

According to an alternative embodiment of the invention, it will be appreciated that the processing performed by the eligibility verification computer 110 could instead be performed by the coordination of benefits application 180. In this alternative embodiment, the coordination of benefits application 180 may have access to aggregate payer information stored in data storage device 182. Thus, the coordination of benefits application 180 may identify one or more payers for a patient by utilizing the aggregate payer information and matching according to certain patient information.

The coordination of benefits application 180 may analyze the healthcare transaction request 210 and the eligibility response 214 to determine whether the patient is associated with more than one payer. If the patient is not associated with more than one payer, then only a single healthcare claim request may be generated and processed. It will be appreciated that the patient may not be associated with more than one payer in the following example scenarios: (i) the healthcare transaction request 210 identifies a single payer, and the eligibility verification computer 110 identifies no additional payers, (ii) the healthcare transaction request 210 identifies no payer, and the eligibility verification computer 110 identifies only a single payer.

On the other hand, the patient may be associated with more than one payer. It will be appreciated that the patient may be associated with more than one payer in any of the following example scenarios: (i) the healthcare transaction request 210 identifies a single payer, and the eligibility verification computer 110 identifies one or more additional payers, (ii) the healthcare transaction request 210 identifies no payers, and the eligibility verification computer 110 identifies two or more payers, (iii) the healthcare transaction request 210 identifies two or more payers, and the eligibility verification computer 110 identifies no payers, or (iv) the healthcare transaction request 210 identifies two or more payers, and the eligibility verification computer 110 identifies one or more payers.

Where there are two or more payers associated with the patient, a prioritization, ordering, or ranking of the two or more payers may be used to identify an order for submitting claim requests (e.g., primary claim request, COB claim request, etc.) to the identified plurality of payers. The prioritization, ordering, or ranking may be directly specified by identifiers in the eligibility response 214 and/or the healthcare transaction request 210. Alternatively, or additionally, the coordination of benefits application 180 may also determine the prioritization, ordering, or ranking of payers based on one or more prioritization rules. A wide variety of prioritization rules may be utilized as desired. For example, a commercial or private payer like an insurance company or pharmacy benefits manager (PBM) may be ordered before a government payer like Medicaid and Medicare. Thus, a commercial or private payer may be prioritized, ordered, or ranked as a first payer while a government payer like Medicaid or Medicare may be prioritized, ordered, or ranked as a second payer, where a claim request may be provided to the first payer for adjudication before another claim request is provided to the second payer for adjudication. As another example, the commercial or private insurance provider may be prioritized, ordered, or ranked before a supplemental insurance provider. As yet another example, information associated with previous healthcare claim transactions processed on behalf of the patient may be accessed from one or more suitable data storage devices, such as data storage devices 182 illustrated in FIG. 1, and an priority, order, or rank utilized in a portion or all of the previous transactions may be utilized in the determination of a prioritization or an ordering of payers.

The COB application 180 may generate or build a primary claim request 220 based upon the first payer identified by the prioritization, order, or rank. The primary claim request 220 may include at least a portion of the information included in the healthcare transaction request 210 and/or eligibility response 214, for example, patient information and information associated with the first payer or first insurance provider. The primary claim request 220, or a copy of the primary claim request 220, may be communicated to service provider computer 106 for routing or communication to an appropriate claims processor computer 108 associated with the primary claim request 220. The primary claim request 220 and/or a copy of the primary claim request 220 may then be routed or otherwise communicated by the service provider computer 106 to the appropriate claims processor computer 108a for adjudication. According to an example embodiment, the service provider computer 106 may utilize at least a portion of the information included in the primary claim request 220, such as a BIN/PCN, to determine the appropriate claims processor computer 108a to route the primary claim request 220 to. The service provider computer 106 may also include a routing table, perhaps stored in memory, for determining which claims processor computer to route the primary claim request 220.

The first claims processor computer 108*a* may receive and adjudicate or otherwise process the primary claim request 220. For example, the first claims processor computer 108*a* may determine benefits coverage for the primary claim request 220 according to an adjudication process associated with eligibility, pricing, and/or utilization review. The first claims processor computer 108*a* may transmit a first adjudicated reply 225 for the primary claim request 220 to the service provider computer 106. The service provider computer 106 may receive the first adjudicated reply 225 from the first claims processor computer 108*a*. As desired, the service provider computer 106 may perform any number of post-edits on the adjudicated reply. For example, the service provider computer 106 may identify the first adjudicated reply 225 as an adjudicated reply for the COB application 180, and the service provider computer 106 may communicate the first adjudicated reply 225 or a copy of the first adjudicated reply 225 to the COB application 180. A wide variety of various identifiers and/or identification techniques may be utilized by the service provider computer 106 to identify the first adjudicated reply 225 as an adjudicated reply for the COB application 180, for example, identification of a claim number by the service provider computer 106.

Assuming that there is more than one payer associated with the patient, the COB application 180 may receive the first adjudicated reply 225, and the COB application 180 may generate or build a coordination of benefits (COB) claim request 230 based at least in part on the information included in the first adjudicated reply 225. An amount paid or authorized for the first adjudicated reply 225 may be determined by the COB application 180, and the determined amount may be utilized in the generation of the COB claim request 230. For example, if the first adjudicated reply 225 indicates that all but a patient responsibility amount (e.g., a $15 or $20 co-pay or co-insurance amount) has been paid or authorized, then the COB claim request 230 may be generated to request a portion or entire patient responsibility amount. As another example, if the first adjudicated reply 225 indicates that the primary claim request has been denied, then the COB claim request 230 may be generated to request a portion or entire claim amount that was included in the primary claim request 220. In this regard, the COB application 180 may attempt to obtain a highest possible payment for the healthcare transaction request 210.

The COB claim request 230 (or a copy of the COB claim request 230) may be communicated to service provider computer 106 for routing or communication to an appropriate claims processor computer 108*b* associated with the COB claim request 230. The COB claim request 230 and/or a copy of the COB claim request 230 may then be routed or otherwise communicated by the service provider computer 106 to the appropriate claims processor computer 108*b* for adjudication. According to an example embodiment, the service provider computer 106 may utilize at least a portion of the information included in the COB claim request 230, such as a BIN/PCN, to determine the appropriate claims processor computer 108*b* to route the COB claim request 230 to. The service provider computer 106 may also include a routing table, perhaps stored in memory, for determining which claims processor computer to route the COB claim request 230 to.

The second claims processor computer 108*b* may receive and adjudicate or otherwise process the COB claim request 230. For example, the second claims processor computer 108*b* may determine benefits coverage for the COB claim request 230 according to an adjudication process associated with eligibility, pricing, and/or utilization review. The second claims processor computer 108*b* may transmit a second adjudicated reply 235 for the COB claim request 230 to the service provider computer 106. The service provider computer 106 may receive the second adjudicated reply 235 from the second claims processor computer 108*b*, and the service provider computer 106 may identify the second adjudicated reply 235 as an adjudicated reply for the COB application 180. The service provider computer 106 may communicate the second adjudicated reply 235 or a copy of the second adjudicated reply 235 to the COB application 180.

The COB application 180 may receive and process the second adjudicated reply 235. The COB application 180 may determine an amount paid or authorized for the second adjudicated reply 235. In this regard, the COB application 180 may determine whether a total amount for the healthcare transaction request 210 has been paid or authorized. If a total amount has not been paid or authorized for payment, then the COB application 180 may determine whether any additional payers (and/or associated claims processor computers) are available. If an additional payer is available, then the COB application 180 may generate an additional COB claim request (e.g., a third claim request) based upon the information included in the second adjudicated reply 235 and the first adjudicated reply 225. The additional COB claim request may then be routed to a claims processor computer 108*a-n* in a similar manner as that utilized to route the other claim requests 220, 230, and an adjudicated reply may be received for the additional secondary claim request. As desired, the COB application 180 may continue to generate or build claim requests until a maximum receivable or maximum available amount for the healthcare transaction request 210 is paid or authorized or until no more payers (or claims processor computers) are available.

Once the adjudication of each claim request generated for the payers has been completed, the COB application 180 may generate or build a single transaction adjudicated reply 240 for the healthcare transaction request 210. The single reply 240 may be generated utilizing each of the adjudicated replies received from various claims processor computers. The single reply 240 or multi-claim reply may include a wide variety of information, for example, information associated with each of the claim requests that have been generated for the healthcare transaction request, information associated with each of the received adjudicated replies, payment information for the various claim requests, a total amount paid or authorized (if applicable), etc. The single reply 240 or a copy of the single reply 240 may be communicated to the service provider computer 106, and the service provider computer 106 may route or otherwise communicate the single reply 240 to the healthcare provider computer 104 as a response to the healthcare transaction request 210. As an alternative to communicating a single reply 240, one or more of the received adjudicated replies may be communicated to the healthcare provider computer 104. These adjudicated replies may be communicated as a single communication or message or as any number of separate communications.

Figure 3:
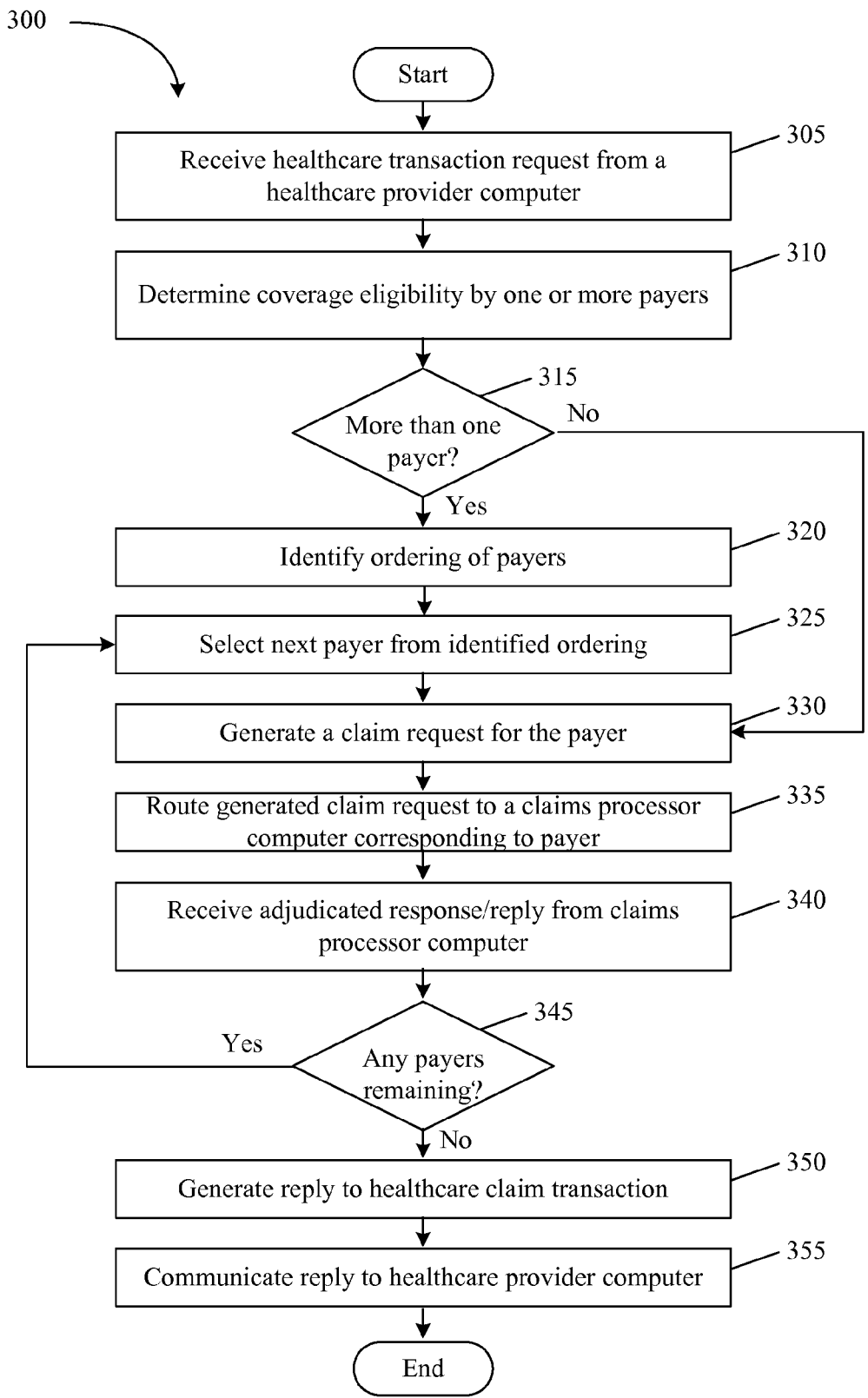
FIG. 3 is a flow chart of an example method for coordination of benefits in healthcare transactions, according to an example embodiment of the invention.

FIG. 3 is a flow chart of an example method 300 for coordination of benefits in healthcare transactions, according to an example embodiment of the invention. The method 300 may be performed by a suitable service provider computer and/or an associated coordination of benefits application, such as the service provider computer 106 and the COB application 180 illustrated in FIG. 1. The method 300 may begin at block 305.

At block 305, the service provider computer 106 may receive a healthcare transaction request from a healthcare provider computer, such as the healthcare provider computer 104 illustrated in FIG. 1. The received healthcare transaction request may be in the form of a healthcare claim request or an eligibility verification request. Thus, the healthcare transaction request may include at least patient or claim information (e.g., identification of drug product, quantity dispensed, days supply, pricing information, etc.), as described herein. As also described herein, the healthcare transaction request can include additional information, including identification of at least one payer, according to an example embodiment of the invention.

At block 310, the service provider computer 106 may identify the healthcare transaction request as being an eligibility verification request or otherwise requesting eligibility verification. A wide variety of identifiers and/or identification techniques, such as the recognition of an other coverage code value (e.g., an OCC value of nine) or some other identifier, may be utilized to identify the received transaction as an eligibility verification request or otherwise requesting eligibility verification. Based upon such an identification, the service provider computer 106 may communicate a copy of the transaction request, or information associated with the transaction request to the COB application 180 for processing. The COB application 180 may generate an eligibility verification request that includes at least the patient information from the healthcare transaction request. The eligibility verification request can be delivered to an eligibility verification computer 110 for processing. If the eligibility verification computer 110 identifies one or more payers available for the patient, then the eligibility verification computer 110 may provide an eligibility response that identifies the one or more payers. For example, the one or more payers may be identified in the eligibility response according to one or both of a respective name or a BIN/PCN number. The eligibility response may also identify a priority, ordering, or ranking among the payers if more than two payers are identified. The priority, ordering, or ranking may be used to determine an order in which claim requests are generated and processed by the two or more identified payers. On the other hand, if the eligibility verification computer 110 cannot identify any payers associated with the patient, then the eligibility response received by the COB application 180 may reflect that no payers have been identified for the patient. In an alternative embodiment of the invention, the COB application 180 may perform similar processing and the eligibility verification computer 110 may not be needed. In another alternative embodiment, the COB application 180 may send eligibility verification requests to multiple eligibility verification computers 110, and thus, multiple eligibility responses may be received.

At block 315, the coordination of benefits application 180 may analyze the healthcare transaction request and the eligibility response, as described herein, to determine whether the patient is associated with more than one payer. If the patient is determined to not be associated with more than one payer at block 315, then processing may proceed to blocks, 330, 335, 340, and 345, where only a single healthcare claim request may be generated, routed to a claims processor computer, and adjudicated by the claims processor computer. On the other hand, the patient may be associated with more than one payer at block 315 in which case processing may proceed to block 320.

At block 320, a prioritization, ordering, or ranking of the two or more payers may be used to identify an order for submitting claim requests (e.g., primary claim request, COB claim request, etc.) to the identified plurality of payers. The prioritization, ordering, or ranking may be directly specified by identifiers in the eligibility response and/or the healthcare transaction request. Alternatively, or additionally, the coordination of benefits application 180 may also determine the prioritization, ordering, or ranking of payers based on one or more prioritization rules. A wide variety of prioritization rules may be utilized as desired. For example, a commercial or private payer like an insurance company or pharmacy benefits manager (PBM) may be ordered before a government payer like Medicaid and Medicare. As another example, the commercial or private insurance provider may be prioritized, ordered, or ranked before a supplemental insurance provider. As yet another example, information associated with previous healthcare claim transactions processed on behalf of the patient may be accessed from one or more suitable data storage devices, such as data storage devices 182 illustrated in FIG. 1, and a priority, order, or rank utilized in a portion or all of the previous transactions may be utilized in the determination of a prioritization or an ordering of payers.

Following block 320 is block 325. At block 325, the next payer based upon the prioritization, ordering, or ranking of the payers at block 320 may be selected. A claim request for the selected component may then be generated or built at block 330. The claim request may be generated utilizing information included in the healthcare transaction request, information included in previously generated claim requests for the transaction, and/or information included in adjudicated replies received for previously generated claim requests. In this regard, a claim request generated for a first payer (or first claims processor computer) may be generated or built utilizing information included in the healthcare transaction request. One or more additional coordination of benefits (COB) claim requests generated for subsequent payers may be generated or built utilizing information from the healthcare transaction request and/or adjudication information received for previous claim requests.

At block 335, the generated claim request at block 330 may be routed or otherwise communicated to an appropriate claims processor computer, such as one of the claims processor computers 108a-n illustrated in FIG. 1 for adjudication. The one of the claims processor computers 108a-n may adjudicate the claim request and communicate and adjudicated reply for the claim request to the service provider computer 106. The adjudicated reply may indicate whether or not the healthcare claim request has been paid. Additionally, if the claim has been paid, the adjudicated reply may include payment information for the claim, including but not limited to, an amount paid or authorized by the claims processor and/or a designated patient responsibility amount (e.g., a patient co-pay amount or co-insurance amount).

The adjudicated reply may be received by the service provider computer 106 at block 340. At block 345, a determination may be made as to whether or not the last payer according to any prioritization, ordering, or ranking has been reached or processed. If it is determined at block 345 that the last payer has not been reached, then operations may continue at block 325, and the next payer may be selected and processed accordingly. In this regard, the COB application 180 may generate a plurality of claim requests in a serial or iterative manner based upon the adjudication of previously processed claims. If, however, it is determined at block 345 that the last payer has been reached, then operations may continue at block 350.

At block 350, a single reply to the healthcare transaction request may be generated or built based upon received adjudicated replies for each of the claim requests that were generated for respective payers. The single reply may then be routed or otherwise communicated to the healthcare provider computer 104 by the service provider computer at block 355. As an alternative to generating and communicating a single reply, each of the received adjudicated replies may be communicated to the healthcare provider computer 104 in any number of suitable communications or messages.

The method 300 may end following block 355.

Figure 4:
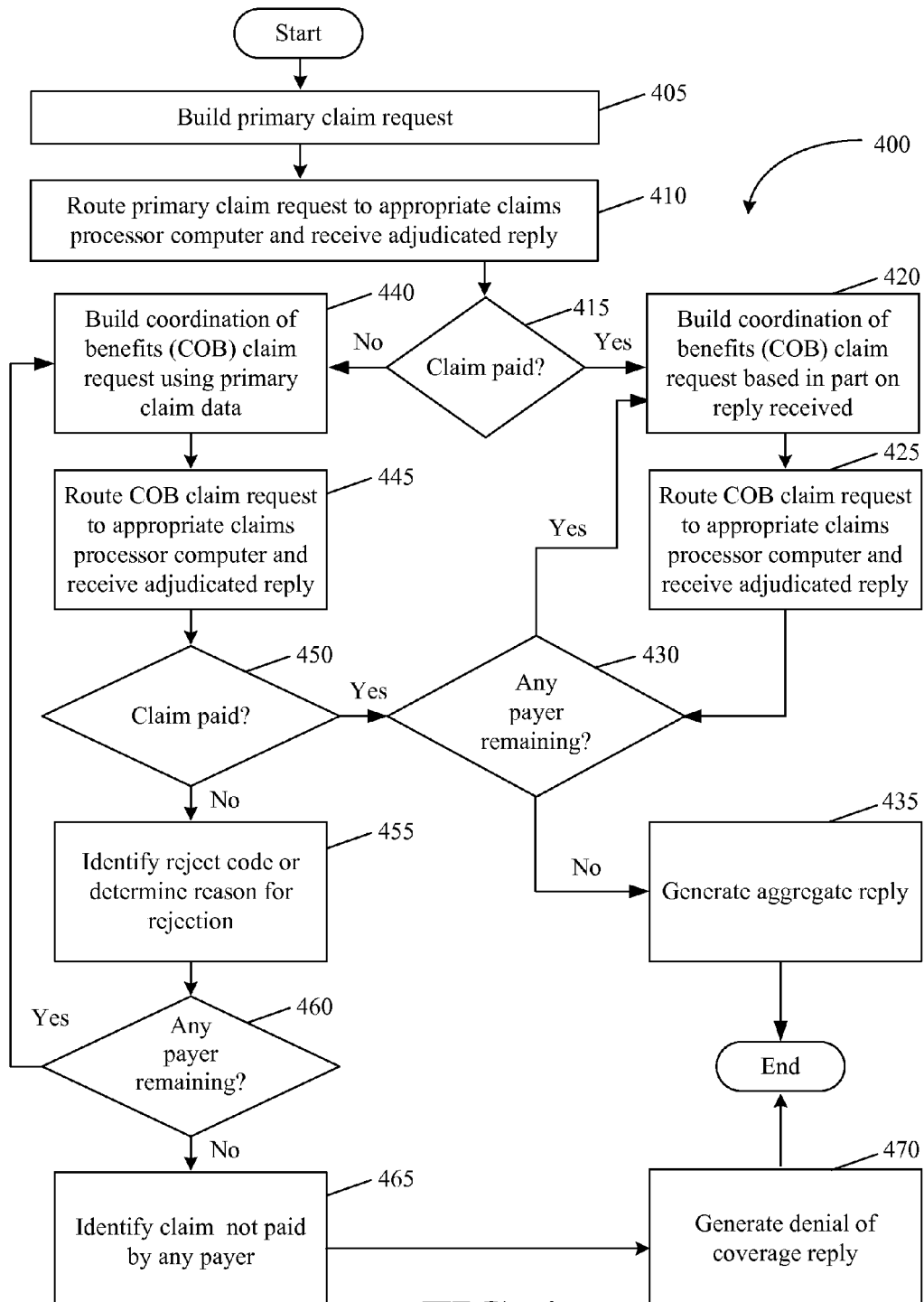
FIG. 4 is a flow chart of an example method for generating claim requests during the coordination of benefits, according to an example embodiment of the invention.

According to an aspect of the invention, a generated claim request for a healthcare transaction request may be based upon one or more previously adjudicated claim requests. FIG. 4 is a flow chart of an example method 400 for generating claim requests during the coordination of benefits, according to an example embodiment of the invention. The method may be performed by a suitable service provider computer and/or an associated coordination of benefits application, such as the service provider computer 106 and COB application 180 illustrated in FIG. 1. The method may facilitate the generation of a primary claim request and one or more coordination of benefits (COB) claim requests for a healthcare transaction request. The method may begin at block 405.

Prior to block 405, a healthcare transaction request may have been initially received by the service provider computer 106 and provided to the coordination of benefits application 180 for processing. The coordination of benefits application 180 may have provided an eligibility verification request to the eligibility verification computer 110 and received an eligibility response. Based upon the eligibility response and/or the healthcare transaction request, the coordination of benefits application 180 may have determined that one or more payers may be available for the patient identified by the healthcare transaction request. Using any determined prioritization, ordering, or ranking determined for the payers, a first payer of the payers can be selected. A primary claim request can then be generated for the first payer, or a claims processor computer associated with the first payer, as illustrated by block 405. The primary claim request may include a portion of the information included in the healthcare transaction request and/or, for example, information associated with the primary payer or primary insurance provider. The primary claim request may additionally request payment for at least a portion of the healthcare transaction request.

At block 410, the primary claim request may be routed or otherwise communicated to an appropriate first payer/claims processor computer associated with the primary claim request. The primary claim request may be adjudicated by the recipient claims processor computer, and an adjudicated reply for the primary claim request may be received at block 410.

At block 415, a determination may be made as to whether the primary claim request has been paid or approved for payment. If it is determined at block 415 that the primary claim request has not been paid, then operations may continue at block 440 which is discussed in greater detail below. If, however, it is determined at block 415 that the primary claim request has been paid, then operations may continue at block 420.

At block 420, a coordination of benefits (COB) claim request may be generated or built based at least in part on the payment that has been made or authorized for the approved primary claim request. For example, a remaining patient responsibility amount following payment of the primary claim request may be identified, and the patient responsibility amount may be requested in the generated COB claim request. As another example, a payment amount for the primary claim request may be subtracted from a total amount provided by the healthcare transaction request, and a portion or all of the remainder may be requested in the generated COB claim request. At block 425, the COB claim request may be routed or otherwise communicated to an appropriate claims processor computer associated with the COB. The COB claim request may be adjudicated by the recipient claims processor computer, and an adjudicated reply for the COB claim request may be received at block 425. Following the receipt of the adjudicated reply for the COB claim request, a determination may be made as to whether the COB claim request has been paid. If the COB claim request has not been paid or if the amount paid for the COB claim request does not satisfy a total outstanding amount for the healthcare transaction request, then one or more additional COB claim requests may be generated.

For example, at block 430, a determination may be made as to whether another payer for the patient is available. If it is determined at block 430 that another payer is available, then operations may continue at block 420 and another COB claim request may be generated based upon the adjudication of prior claim requests. If, however, it is determined at block 430 that another payer is not available, then operations may continue at block 435. At block 435, an aggregate reply for the healthcare transaction request may be generated based upon the adjudication of each of the claim requests. As desired, the aggregate reply may then be routed or otherwise communicated to the healthcare provider computer.

At block 440, which may be reached if it is determined at block 415 that the primary claim request has not been paid, a COB claim request may be generated or built utilizing data for the rejected primary claim request. For example, the COB claim request may request an entire amount for the healthcare transaction request or an amount minus a patient responsibility amount. The COB claim request may be generated for submission to a different claims processor computer, for example, a different insurance provider or other payer. At block 445, the generated COB claim request may be routed or otherwise communicated to an appropriate claims processor computer associated with the COB claim request. The COB claim request may be adjudicated by the recipient claims processor computer, and an adjudicated reply for the secondary claim request may be received at block 445.

Following the receipt of the adjudicated reply for the COB claim request, a determination may be made at block 450 as to whether the COB claim request has been paid. If it is determined at block 450 that the COB claim request has been paid, then operations may continue at block 430 as discussed above. If, however, it is determined at block 450 that the COB claim request has not been paid, then operations may continue at block 455.

At block 455, which may be optional in certain embodiments of the invention, a reject code may be identified for the COB claim request or a reason for rejection or denial of the COB claim request may be determined. A wide variety of rejection codes may be identified for the COB claim request, for example, a code indicating that the provider is not covered, a code indicating that the patient is not covered, or a code indicating that the payment was not collected. Additionally, although the determination of a reject code is described above with reference to a rejected COB claim request following the rejection of a primary claim request, it will be appreciated that a rejection code may be identified for any rejected claim request. These rejection codes may then be included in a generated reply.

At block 460, a determination may be made as to whether another payer is available. If it is determined at block 460 that another payer is available for the patient, then operations may continue at block 440, and another COB claim request may be generated utilizing the primary claim data. If, however, it is determined at block 460 that another payer is not available for the patient, then operations may continue at block 465. At block 465, the healthcare transaction request may be identified as a denied or unpaid claim transaction. A reply to the healthcare transaction request indicating that the claim is denied may be generated for communication to the healthcare provider computer 104 at block 470. The generated reply may be a relatively simple reply identifying the healthcare transaction request as unpaid or, alternatively, may be a single or multi-claim reply that includes information associated with the adjudication of each of the generated claim requests.

The method 400 may end following block 435 or block 470.

The operations described and shown in the methods 300 and 400 of FIGS. 3 and 4, respectively, may be carried out or performed in any suitable order as desired in various embodiments of the invention. Additionally, in certain embodiments, at least a portion of the operations may be carried out in parallel. Furthermore, in certain embodiments, less than or more than the operations described in FIGS. 3 and 4 may be performed.

Figure 2B:
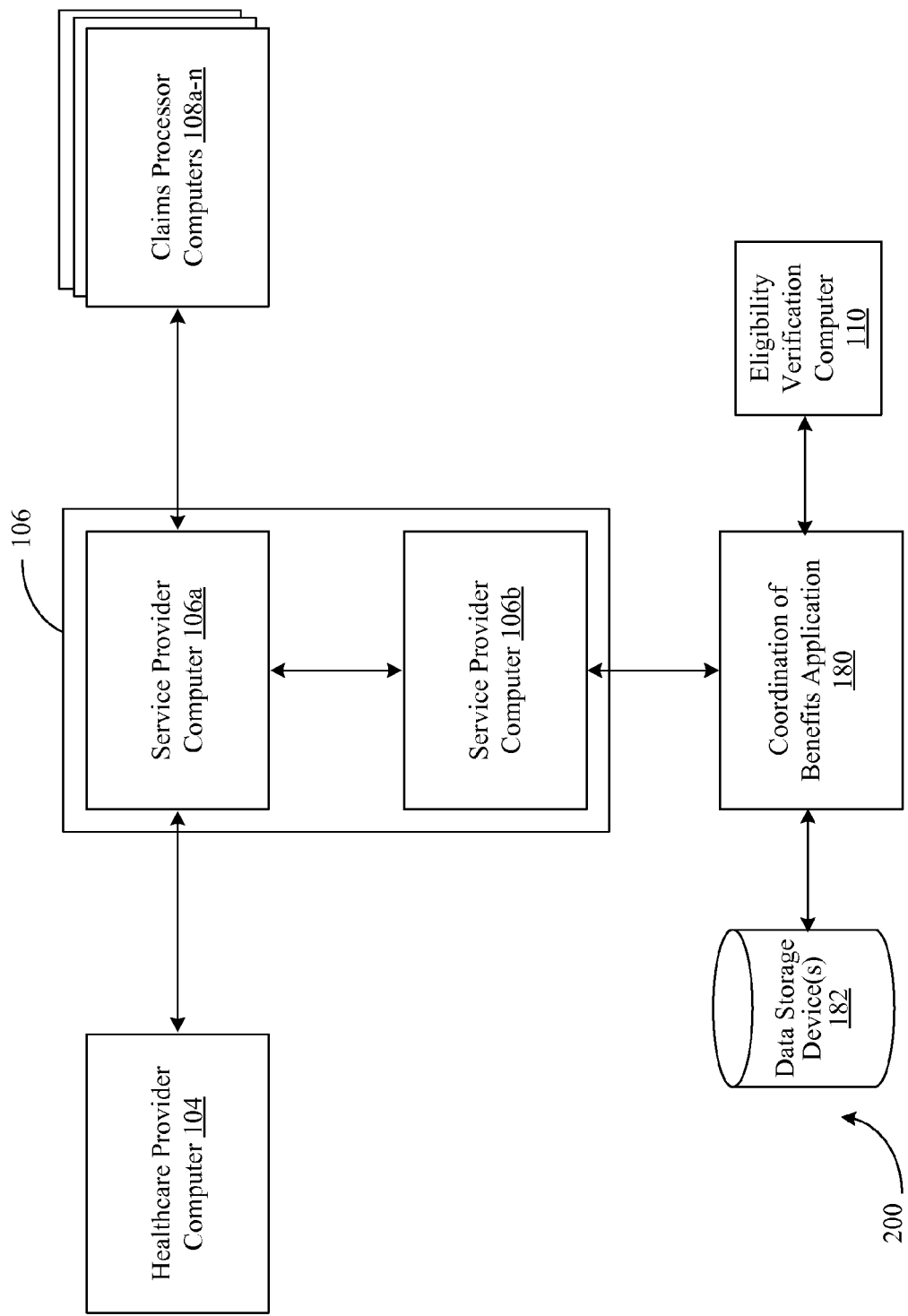

It will be appreciated that variations of FIG. 2B may be utilized in accordance with various embodiments of the invention. For example, as shown in FIG. 2B, the service provider computer 106 may be comprised of two or more distinct service provider computers 106a and 106b that are in communication with each other. Service provider computer 106a may be operative with one or more healthcare provider computers and claims processor computers, such as the healthcare provider computer 104 and claims processor computer 108 illustrated in FIG. 1. However, service provider computer 106b may have a data processing arrangement with service provider computer 106a. Under the data processing agreement, the service provider computer 106a may be permitted to utilize or offer services of the service provider computer 106b, including those of the coordination of benefits application 180. For example, a first service provider may communicate claims and/or other information to a second service provider for processing.

Example Financial Illustration of Coordination of Benefits

An example illustration of a financial impact of processing multiple claim requests in accordance with an example coordination of benefits in healthcare transactions will now be discussed. For example, a healthcare request may be delivered from a healthcare provider computer to the service provider computer that identifies a patient as well as a product for the patient. The healthcare request may identify a pharmacy financial request of $100.00 for payment of the product. The service provider computer, either alone or in conjunction with an eligibility verification computer, may determine that the patient is associated with three payers. Based upon a priority, ordering, or ranking of the three payers, a first payer will be identified as the primary payer. Accordingly, a primary claim request will be generated and delivered to a first claims processor computer associated with the primary payer. The primary claim request may identify the patient, the product, and the pharmacy financial request of $100. The first claims processor computer may adjudicate the primary claim request. For example, primary payer may have a 90% contracted payment amount with the pharmacy, and thus, the pharmacy may receive a total of $90 ($100*0.90=$90). However, the patient responsibility amount may be $10, thereby leaving a primary payer amount of $80 ($90−$10=$80). Thus, the first claims processor computer may deliver a primary claim response that indicates the primary payer payment amount of $80 along with a patient responsibility amount of $10.

Since there is another payer available, a second payer will be identified. A first COB claim request may be generated and delivered to a second claims processor computer associated with the second payer. The first COB claim request may identify the patient, the product, and an Other Coverage Code (OCC). For example, in accordance with an NCPDP standard, the OCC code may be "2" (Other coverage exists—payment collected). In this case, the first COB claim request would also include the pharmacy financial request of $100 along with the Payment Amount of $80 collected from the primary payer. The second claims processor computer may adjudicate the first COB claim request. For example, the secondary payer may have a 95% contracted payment amount with the pharmacy, and thus, the pharmacy may receive a total of $95 ($100*0.95=$95). However, this $95 amount will be reduced by the $80 payment paid by the primary payer, thereby leaving a contracted payment amount of $15 to be covered by the second payer. The patient responsibility may be deducted from the remaining balance. Thus, if the patient responsibility amount remains as $10 under the patient benefit, the second payer amount will be $5 since the OCC code of "2" is used to obtain payments for the pharmacy.

However, in some instances, another OCC code besides 2" (Other coverage exists—payment collected) can be utilized. For example, an OCC code of "8" (claim is billing for a copay) can be utilized. Thus, assuming that the third payer (e.g., a government payer) is available to cover at least a portion of the payment responsibility amount, then a second COB claim request can be generated and delivered to a third claims processor computer associated with the third payer. The second COB claim request may identify the patient, the product, and an Other Coverage Code (OCC) of "8". Accordingly, the second COB claim request may identify the patient responsibility amount of $10. The second claims processor computer may adjudicate the second COB claim request, and determine that $8 of the $10 patient responsibility amount is covered. Thus, the second COB claim response will indicate that the patient responsibility amount is $2 ($10−$8=$2).

Since no additional payers remain, the service provider computer can prepare a single aggregated reply to the healthcare request. Given that the first payer paid $80, the second payer paid $5, and the third payer paid $8, the total paid amount from the payers is $93. The patient responsibility amount is $2. Thus, the single aggregated reply delivered to the healthcare provider computer would reflect a paid amount of $93 along with a patient responsibility amount of $2.

It will be appreciated that the example financial illustrations presented above are by way of example only. Indeed, there may be an almost infinite number of example financial illustrations available in accordance with example embodiments of the invention.

Example embodiments of the invention can provide the technical effects of creating a system, method, and apparatus that coordinates benefits for healthcare claim transactions associated with a healthcare transaction request. Additionally, example embodiments of the invention can provide the technical effect of generating and adjudicating a plurality of claim requests resulting from a single healthcare transaction request, with the communication of a single reply to a healthcare provider computer. In this regard, healthcare providers can streamline their workflows, and reduce errors associated with traditional coordination of benefits processing.

Various block and/or flow diagrams of systems, methods, apparatuses, and/or computer program products according to example embodiments of the invention are described above.

It will be understood that one or more blocks of the block diagrams and flow diagrams, and combinations of blocks in the block diagrams and flow diagrams, respectively, can be implemented by computer-executable program instructions. Likewise, some blocks of the block diagrams and flow diagrams may not necessarily need to be performed in the order presented, or may not necessarily need to be performed at all, according to some embodiments of the invention.

These computer-executable program instructions may be loaded onto a special purpose computer or other particular machine, a processor, or other programmable data processing apparatus to produce a particular machine, such that the instructions that execute on the computer, processor, or other programmable data processing apparatus create means for implementing one or more functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instruction means that implement one or more functions specified in the flow diagram block or blocks. As an example, embodiments of the invention may provide for a computer program product, comprising a computer-usable medium having a computer-readable program code or program instructions embodied therein, said computer-readable program code adapted to be executed to implement one or more functions specified in the flow diagram block or blocks. The computer program instructions may also be loaded onto a computer or other programmable data processing apparatus to cause a series of operational elements or steps to be performed on the computer or other programmable apparatus to produce a computer-implemented process such that the instructions that execute on the computer or other programmable apparatus provide elements or steps for implementing the functions specified in the flow diagram block or blocks.

Accordingly, blocks of the block diagrams and flow diagrams support combinations of means for performing the specified functions, combinations of elements or steps for performing the specified functions, and program instruction means for performing the specified functions. It will also be understood that each block of the block diagrams and flow diagrams, and combinations of blocks in the block diagrams and flow diagrams, can be implemented by special-purpose, hardware-based computer systems that perform the specified functions, elements or steps, or combinations of special purpose hardware and computer instructions.

Many modifications and other embodiments of the invention set forth herein will be apparent having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A computer-implemented method, comprising:
    receiving a healthcare claim request from a healthcare provider computer, the healthcare claim request including patient information identifying a patient, and product information identifying a product for the patient;
    determining, based at least in part from a portion of the patient information in the healthcare transaction claim request, that the patient is associated with at least a first payer and a second payer, wherein the determining includes:
        transmitting an eligibility request to an eligibility verification computer, the eligibility request including at least a portion of the patient information in the healthcare transaction claim request, and
        receiving, from the eligibility verification computer, an eligibility reply that identifies at least two payers associated with the patient, wherein the eligibility reply includes respective cardholder identifiers for the at least two payers, wherein the cardholder identifiers identify the account holder for each respective payer, wherein the cardholder identifiers are different for each respective payer,
        wherein the respective cardholder identifiers for the at least two payers are utilized to determine which of the at least two payers is the first payer or the second payer;
    generating a primary claim request based upon the identified product and the patient associated with the healthcare claim request, the primary claim associated with the first payer;
    communicating the generated primary claim request to a first claims processor computer associated with the first payer for adjudication;
    receiving, from the first claims processor computer, a first adjudicated reply for the primary claim, the first adjudicated reply indicating first financial coverage information for the identified product for the patient;
    generating a coordination of benefits (COB) claim request based at least in part on the received first adjudicated reply, the COB claim request including at least a portion of the first financial coverage information for the identified product, the COB claim request associated with a second payer;
    communicating the generated COB claim request to a second claims processor computer associated with the second payer for adjudication;
    receiving, from the second claims processor computer, a second adjudicated reply for the COB claim; and
    communicating information associated with the first adjudicated reply and the second adjudicated reply to the healthcare provider computer,
    wherein the above operations are performed by one or more computers associated with a service provider.

2. The computer-implemented method of claim 1, further comprising:
    ordering the respective at least two payers in a sequence; and
    identifying the first and second payers from the at least two payers according to the sequence,
    wherein the above operations are performed by one or more computers associated with the service provider.

3. The computer-implemented method of claim 1, wherein the patient is determined to be associated with the first payer, the second payer, and a third payer, wherein the coordination of benefits (COB) claim request is a first COB claim request, wherein the second adjudicated reply indicates second financial coverage information for the identified product for the patient, and further comprising:
    generating a second coordination of benefits (COB) claim request based at least in part on one or both of the received first adjudicated reply or the second adjudicated reply, the second COB claim request including at least a portion of one or both of the first or second financial coverage information, the second COB claim request associated with a third payer;

communicating the generated second COB claim request to a third claims processor computer associated with the third payer for adjudication;

receiving, from the third claims processor computer, a third adjudicated reply for the second COB claim;

aggregating at least a portion of the first adjudicated reply, the second adjudicated reply, and the third adjudicated reply into a single response for the healthcare claim request; and communicating the single response to the healthcare provider computer, wherein the above operations are performed by one or more computers associated with the service provider.

4. The computer-implemented method of claim 1, further comprising:

aggregating at least a portion of the first adjudicated reply and the second adjudicated reply into a single response for the healthcare claim request, wherein communicating information associated with the first adjudicated reply and the second adjudicated reply to the healthcare provider computer comprises communicating the single response to the healthcare provider computer, wherein the above operations are performed by one or more computers associated with the service provider.

5. The computer-implemented method of claim 1, wherein receiving a first adjudicated reply comprises receiving a first adjudicated reply indicating that the primary claim request has been approved by the first claims processor computer, and further comprising:

identifying an amount paid based upon the first financial coverage information for the first adjudicated reply; and determining a second payment amount based at least in part on the identified amount paid for the first adjudicated reply, wherein generating the COB claim request comprises generating the COB claim request utilizing the determined second payment amount, wherein the above operations are performed by one or more computers associated with the service provider.

6. The computer-implemented method of claim 5, wherein determining a second payment amount comprises determining one of a secondary insurance payment amount or a patient responsibility amount.

7. The computer-implemented method of claim 1, wherein:

receiving a first adjudicated reply comprises receiving a first adjudicated reply indicating that the primary claim request has been rejected by the first claims processor computer, wherein the first financial coverage indicates no coverage by the primary payer, and generating a coordination of benefits (COB) claim request comprises generating the COB claim request utilizing at least a portion of the data included in the rejected primary claim request.

8. The computer-implemented method of claim 7, wherein receiving a second adjudicated reply comprises receiving a second adjudicated reply indicating that the COB claim request has been denied by the second claims processor computer, and further comprising:

determining a reject code associated with the denial of the COB claim request, wherein the above operation is performed by one or more computers associated with the service provider.

9. The computer-implemented method of claim 8, further comprising:

determining that the patient is not associated with any other payer other than the first payer and the second payer;

based upon the determination that the patent is not associated with any other payer, identifying the healthcare claim request as a denied healthcare claim request, wherein the above operations are performed by one or more computers associated with the service provider.

10. A system, comprising:

at least one memory operable to store computer-executable instructions; and at least one processor configured to access the at least one memory and execute the computer-executable instructions to:

receive a healthcare claim request from a healthcare provider computer, the healthcare claim request including patient information identifying a patient, and product information identifying a product for the patient;

determine, based at least in part from a portion of the patient information in the healthcare transaction claim request, that the patient is associated with at least a first payer and a second payer by, transmitting an eligibility request to an eligibility verification computer, the eligibility request including at least a portion of the patient information in the healthcare transaction claim request, and receiving, from the eligibility verification computer, an eligibility reply that identifies at least two payers associated with the patient, wherein the eligibility reply includes respective cardholder identifiers for the at least two payers, wherein the cardholder identifiers identify the account holder for each respective payer, wherein the cardholder identifiers are different for each respective payer, and wherein the respective cardholder identifiers for the at least two payers are utilized to determine which of the at least two payers is the first payer or the second payer;

generate a primary claim request based upon the identified product and the patient associated with the healthcare claim request, the primary claim associated with the first payer;

communicate the generated primary claim request to a first claims processor computer associated with the first payer for adjudication;

receive, from the first claims processor computer, a first adjudicated reply for the primary claim, the first adjudicated reply indicating first financial coverage information for the identified product for the patient;

generate a coordination of benefits (COB) claim request based at least in part on the received first adjudicated reply, the COB claim request including at least a portion of the first financial coverage information for the identified product, the COB claim request associated with a second payer;

communicate the generated COB claim request to a second claims processor computer associated with the second payer for adjudication;

receive, from the second claims processor computer, a second adjudicated reply for the COB claim; and communicate information associated with the first adjudicated reply and the second adjudicated reply to the healthcare provider computer.

11. The system of claim 10, wherein the patient is determined to be associated with the first payer, the second payer, and a third payer, wherein the coordination of benefits (COB) claim request is a first COB claim request, wherein the second adjudicated reply indicates second financial coverage information for the identified product for the patient, and wherein the at least one processor is further configured to execute the computer-executable instructions to:
- generate a second coordination of benefits (COB) claim request based at least in part on one or both of the received first adjudicated reply or the second adjudicated reply, the second COB claim request including at least a portion of one or both of the first or second financial coverage information, the second COB claim request associated with a third payer;
- communicate the generated second COB claim request to a third claims processor computer associated with the third payer for adjudication;
- receive, from the third claims processor computer, a third adjudicated reply for the second COB claim,
- aggregate at least a portion of the first adjudicated reply, the second adjudicated reply, and the third adjudicated reply into a single response for the healthcare claim request; and communicating the single response to the healthcare provider computer.

12. The system of claim 10, wherein the at least one processor is further configured to execute the computer-executable instructions to:
- aggregate at least a portion of the first adjudicated reply and the second adjudicated reply into a single response for the healthcare claim request,
- wherein the information associated with the first adjudicated reply and the second adjudicated reply is communicated to the healthcare provider computer by communicating the single response to the healthcare provider computer.

13. The system of claim 10, wherein receiving a first adjudicated reply comprises receiving a first adjudicated reply indicating that the primary claim request has been approved by the first claims processor computer, and wherein the at least one processor is further configured to execute the computer-executable instructions to:
- identify an amount paid based upon the first financial coverage information for the first adjudicated reply; and
- determine a second payment amount based at least in part on the identified amount paid for the first adjudicated reply,
- wherein the COB claim request is generated utilizing the determined second payment amount.

* * * * *